(12) United States Patent
Jen et al.

(10) Patent No.: US 7,307,173 B1
(45) Date of Patent: Dec. 11, 2007

(54) PYRROLINE CHROMOPHORES

(75) Inventors: Kwan-Yue Jen, Kenmore, WA (US); Sei-Hum Jang, Mukilteo, WA (US); Bart Kahr, Seattle, WA (US)

(73) Assignee: University of Washington, Seattle, WA (US)

( * ) Notice: Subject to any disclaimer, the term of this patent is extended or adjusted under 35 U.S.C. 154(b) by 40 days.

(21) Appl. No.: 11/064,420

(22) Filed: Feb. 22, 2005

Related U.S. Application Data

(60) Provisional application No. 60/546,038, filed on Feb. 19, 2004.

(51) Int. Cl.
*C07D 277/20* (2006.01)
*C07D 275/02* (2006.01)
*C07D 409/00* (2006.01)

(52) U.S. Cl. ............... 548/400; 548/202; 548/206; 548/527

(58) Field of Classification Search ............ 548/527, 548/327
See application file for complete search history.

(56) References Cited

U.S. PATENT DOCUMENTS

| | | | | |
|---|---|---|---|---|
| 3,013,013 A | * | 12/1961 | Carboni ............... | 548/468 |
| 4,845,235 A | | 7/1989 | Matumoto et al. | |
| 5,011,811 A | | 4/1991 | Shuttleworth et al. | |
| 5,166,128 A | * | 11/1992 | Shuttleworth et al. ...... | 503/227 |
| 5,660,598 A | * | 8/1997 | Cavanagh et al. ............ | 8/532 |
| 6,589,296 B1 | * | 7/2003 | Leaver et al. ............... | 8/532 |

FOREIGN PATENT DOCUMENTS

| JP | 62216794 A2 | 9/1987 |
|---|---|---|
| JP | 9255883 A | 9/1997 |
| JP | 09255883 | * 2/1999 |

OTHER PUBLICATIONS

Choi et al. "Structure-wet fastness relationships of some blue disperse dyes for polyester," J. of the Soc. of Dyers and Colourists, 119(6), pp. 273-278 (2000).*
Choi et al., STN International, HCAPLUS Database, Columbus, OH, Accession No. 2000:696129.*
Nishigaki et al., STN International, HCAPLUS Database, Columbus, OH, Accession No. 1997:648618.*
Albert, I.D.L., et al., "Large Molecular Hyperpolarizabilites. Quantitative Analysis of Aromaticity and Auxiliary Donor-Acceptor Effects," *J. Am. Chem. Soc. 119*:6575-6582, 1997.
Shu, C.F., and Yuh-Kai Wang, "Synthesis of Nonlinear Optical Chromophores Containing Electron-Excessive and -Deficient Heterocyclic Bridges. The Auxiliary Donor-Acceptor Effects," *J. Mater. Chem. 8*(4):833-835, 1998.
Varanasi, P.R., et al., "The Important Role of Heteroaromatics in the Design of Efficient Second-Order Nonlinear Optical Molecules: Theoretical Investigation on Push-Pull Heteroaromatic Stilbenes," *J. Am. Chem. Soc. 118*:12443-12448, 1996.

* cited by examiner

*Primary Examiner*—Kamal A. Saeed
*Assistant Examiner*—Sun Jae Y Loewe
(74) *Attorney, Agent, or Firm*—Christensen O'Connor Johnson Kindness PLLC

(57) ABSTRACT

Electron acceptor compounds, nonlinear optical chromophores, methods for making the compounds and chromophores, and materials and electro-optic devices that include the chromophores.

8 Claims, 23 Drawing Sheets

*ground state dipole moments were calculated by ZIND INDO/S method using AM1 and DFT in ( ) geometries in the unit of Debye.

wherein at least one of m, n, or o is ≥ 1.

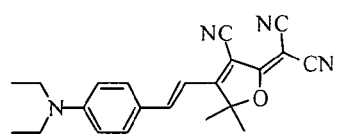

3
$\lambda_{max}$ = 539 nm (dioxane)
$\lambda_{max}$ = 561 nm (toluene) + 22
$\lambda_{max}$ = 584 nm (CHCl$_3$) + 23
$^2\lambda_{max}$ = 23 nm (0.087 eV)
$^2\lambda_{max}$ / MW = 2.43 x 10$^{-4}$ eV

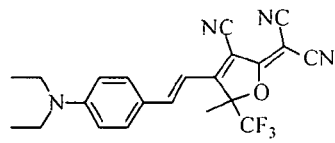

4
$\lambda_{max}$ = 594 nm (dioxane)
$\lambda_{max}$ = 607 nm (toluene) + 13
$\lambda_{max}$ = 628 nm (CHCl$_3$) + 21
$^2\lambda_{max}$ = 21 nm (0.069 eV)
$^2\lambda_{max}$ / MW = 1.67 x 10$^{-4}$ eV

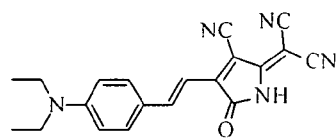

5
$\lambda_{max}$ = 671 nm (dioxane)
$\lambda_{max}$ = 691 nm (toluene) + 20
$\lambda_{max}$ = 732 nm (CHCl$_3$) + 41
$^2\lambda_{max}$ = 41 nm (0.100 eV)
$^2\lambda_{max}$ / MW = 2.91 x 10$^{-4}$ eV

FIGURE 8

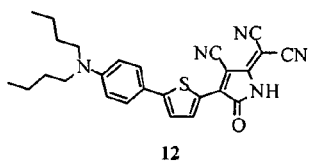 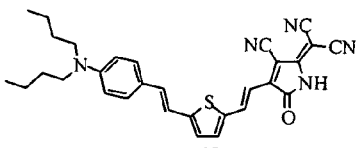 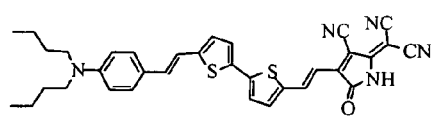

12
$\lambda_{max}$ = 705 nm (dioxane)
$\lambda_{max}$ = 731 nm (toluene) + 26
$\lambda_{max}$ = 780 nm (CHCl$_3$) + 49
$^2\lambda_{max}$ = 49 nm (0.106 eV)
$^2\lambda_{max}$ / MW = 2.33 x 10$^{-4}$ eV

13
$\lambda_{max}$ = 764 nm (dioxane)
$\lambda_{max}$ = 807 nm (toluene) + 43
$\lambda_{max}$ = 875 nm (CHCl$_3$) + 68
$^2\lambda_{max}$ = 68 nm (0.119 eV)
$^2\lambda_{max}$ / MW = 2.34 x 10$^{-4}$ eV

14
$\lambda_{max}$ = 748 nm (dioxane)
$\lambda_{max}$ = 800 nm (toluene) + 52
$\lambda_{max}$ = 838 nm (CHCl$_3$) + 38
$^2\lambda_{max}$ = 38 nm (0.070 eV)
$^2\lambda_{max}$ / MW = 1.19 x 10$^{-4}$ eV

FIGURE 11

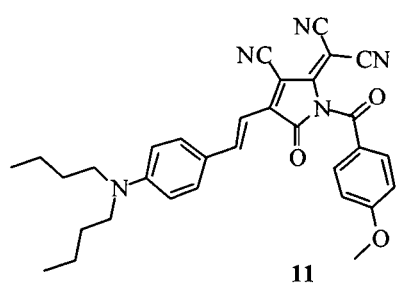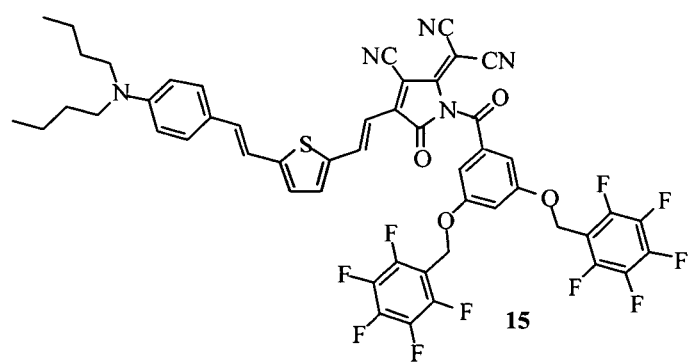
FIGURE 12

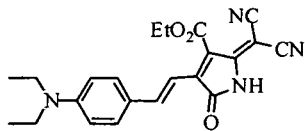
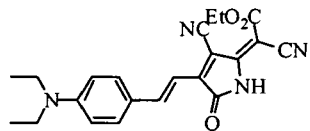
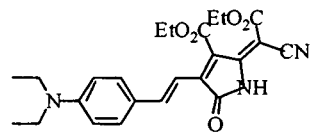
| | | | | | |
|---|---|---|---|---|---|
| $\mu$ | = 11.2 D | $\mu$ | = 11.4 D | $\mu$ | = 11.1 D |
| $\beta_o$ | = 36.4 x 10$^{-30}$ esu | $\beta_o$ | = 34.1 x 10$^{-30}$ esu | $\beta_o$ | = 29.1 x 10$^{-30}$ esu |
| $\beta_{1907\,nm}$ | = 51.1 x 10$^{-30}$ esu | $\beta_{1907\,nm}$ | = 47.9 x 10$^{-30}$ esu | $\beta_{1907\,nm}$ | = 39.9 x 10$^{-30}$ esu |
| $\mu\beta_o$ | = 407.7 x 10$^{-48}$ esu | $\mu\beta_o$ | = 388.7 x 10$^{-48}$ esu | $\mu\beta_o$ | = 323.0 x 10$^{-48}$ esu |
| $\mu\beta_{1907\,nm}$ | = 572.3 x 10$^{-48}$ esu | $\mu\beta_{1907\,nm}$ | = 546.1 x 10$^{-48}$ esu | $\mu\beta_{1907\,nm}$ | = 442.9 x 10$^{-48}$ esu |
| $\lambda_{max}$ | = 412 nm | $\lambda_{max}$ | = 414 nm | $\lambda_{max}$ | = 403 nm |
FIGURE 13

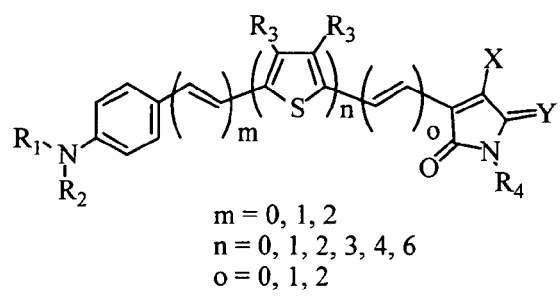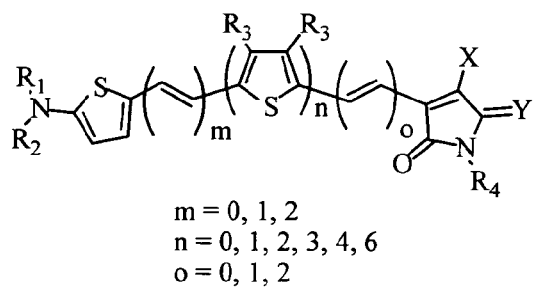
m = 0, 1, 2
n = 0, 1, 2, 3, 4, 6
o = 0, 1, 2
m = 0, 1, 2
n = 0, 1, 2, 3, 4, 6
o = 0, 1, 2
FIGURE 14

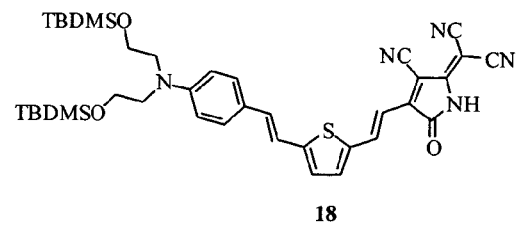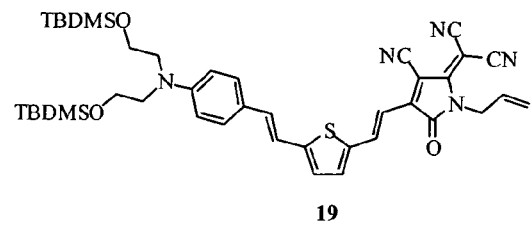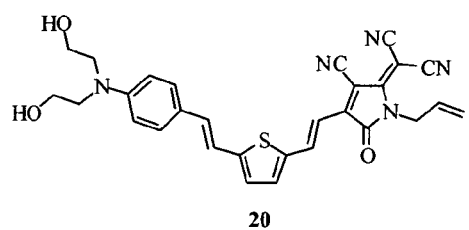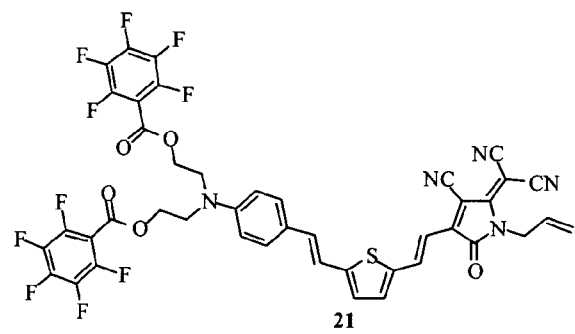
FIGURE 16

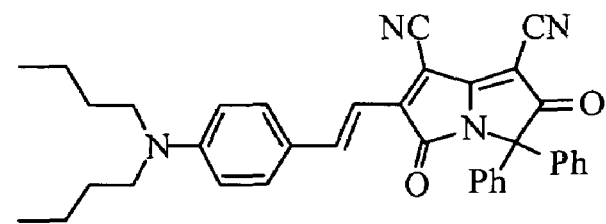
23
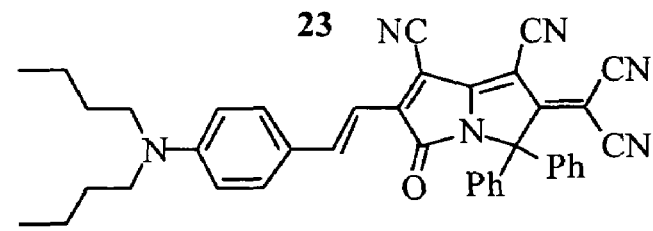
24
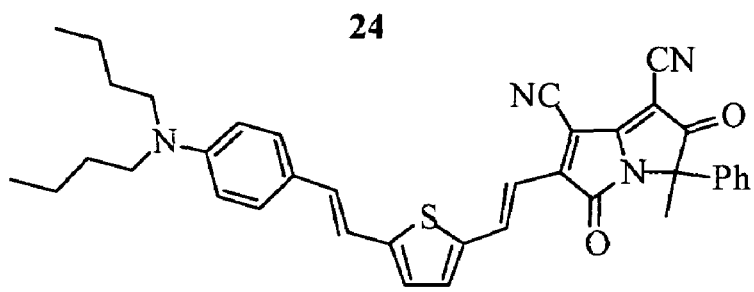
25
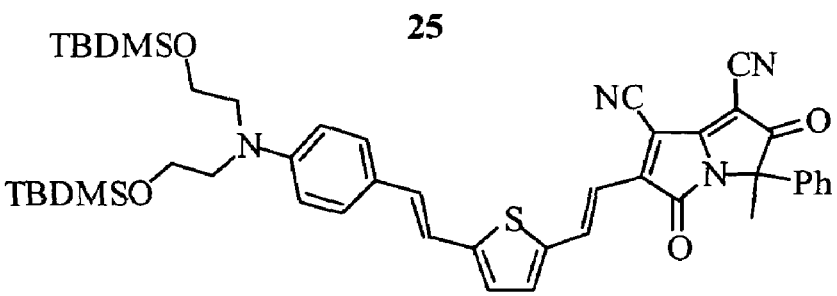
26
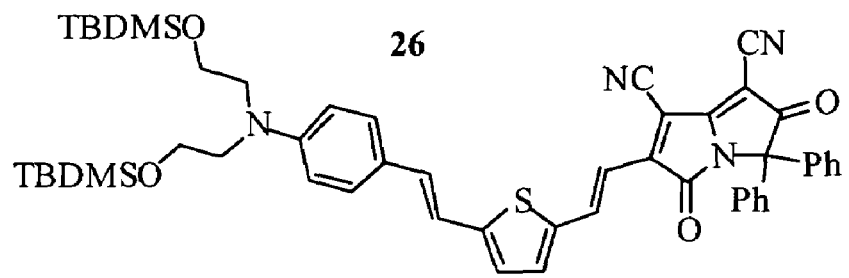
27
FIGURE 22

PYRROLINE CHROMOPHORES

CROSS-REFERENCE TO RELATED APPLICATIONS

This application claims the benefit of U.S. Provisional Application No. 60/546,038, filed Feb. 19, 2004, which is incorporated by reference herein.

STATEMENT OF GOVERNMENT LICENSE RIGHTS

Research leading to the present invention was supported, at least in part, under DMR-0120967 awarded by the National Science Foundation and under MDA972-02-1-0009 awarded by the U.S. Army Medical Research Acquisition Activity. The Government may have certain rights in the invention.

FIELD OF THE INVENTION

The present invention relates to nonlinear optical chromophores that include pyrroline or pyrrolizine electron acceptor groups.

BACKGROUND OF THE INVENTION

Electrical signals can be encoded onto fiber-optic transmissions by electrooptic modulators. These modulators include electro-optic materials having highly polarizable electrons. When these materials are subject to an electric field, their polarization changes dramatically resulting in an increase in the index of refraction of the material and an accompanying decrease in the velocity of light travelling through the material. This electric field-dependent index of refraction can be used to encode electric signals onto optical signals. Uses include, for example, switching optical signals and steering light beams.

A variety of electro-optic materials have been utilized for use in electro-optic devices. Among these materials are inorganic materials such as lithium niobate, semiconductor materials such as gallium arsenide, organic crystalline materials, and electrically-poled polymer films that include organic chromophores. A review of nonlinear optical materials is provided in L. Dalton, "Nonlinear Optical Materials", Kirk-Othmer Encyclopedia of Chemical Technology, 4th Edition, Volume 17 (John Wiley & Sons, New York, 1995), pp. 288.

In contrast to inorganic materials in which polar optical lattice vibrations diminish their effectiveness, the optical properties of organic nonlinear optical materials depend primarily on the hyperpolarizability of their electrons without a significant adverse contribution from the lattice polarizability. Thus, organic nonlinear optical materials offer advantages for ultrafast electro-optic modulation and switching.

Lithium niobate, a common material currently utilized in electro-optic devices, has an electro-optic coefficient of about 35 pm/V resulting in a typical drive voltage of about 5 volts. Drive voltage ($V\pi$) refers to the voltage required to produce a $\pi$ phase shift of light. Lithium niobate has a high dielectric constant ($\epsilon=28$), which results in a mismatch of electrical and optical waves propagating in the material. The mismatch necessitates a short interaction length, which makes drive voltage reduction through increasing device length unfeasible, thereby limiting the device's bandwidth. Recent lithium niobate modulators have been demonstrated to operate at a bandwidth of over 70 GHz.

Electro-optic poled polymers have also been utilized as modulating materials. Their advantages include their applicability to thin-film waveguiding structures, which are relatively easily fabricated and compatible with existing microelectronic processing. These polymers incorporate organic nonlinear optically active molecules to effect modulation. Because organic materials have low dielectric constants and satisfy the condition that $n^2=\epsilon$, where n is the index of refraction and $\epsilon$ is the dielectric constant, organic electro-optic will have wide bandwidths. The dielectric constant of these materials ($\epsilon=2.55-4$) relatively closely matches the propagating electrical and optical waves, which provides for a drive voltage in the range of about 1-2 volts and a bandwidth greater than 1 00 GHz.

Advantages of organic nonlinear optical materials include a bandwidth in excess of 100 GHz/cm device and ease of integration with semiconductor devices. See, L. Dalton et al., "Synthesis and Processing of Improved Organic Second-Order Nonlinear Optical Materials for Applications in Photonics", Chemistry of Materials, Vol. 7, No. 6, pp. 1060-1081 (1995). In contrast to inorganic materials, these organic materials can be systematically modified to improve electro-optic activity by the design and development of new organic materials and by the development of improved processing methods. See, L. Dalton et al., "The Role of London Forces in Defining Noncentrosymmetric Order of High Dipole Moment-High Hyperpolarizability Chromophores in Electrically Poled Polymeric Films", Proceedings of the National Academy of Sciences USA, Vol. 94, pp. 4842-4847 (1997).

For an organic nonlinear optical material to be suitable for electro-optic applications, the material should have a large molecular optical nonlinearity, referred to as hyperpolarizability ($\beta$), and a large dipole moment ($\mu$). A common figure of merit used to compare materials is the value $\mu\beta$. See Dalton et al. (1997). Organic materials having $\mu\beta$ values greater than about $15,000\times10^{-48}$ esu that also satisfy the requirements of thermal and chemical stability and low optical loss at operating wavelengths have only recently been prepared. See Dalton et al., "New Class of High Hyperpolarizability Organic Chromophores and Process for Synthesizing the Same", WO 00/09613. However, materials characterized as having such large $\mu\beta$ values suffer from large intermolecular electrostatic interactions that lead to intermolecular aggregation resulting in light scattering and unacceptably high values of optical loss. See Dalton et al. (1997).

Thus, the effectiveness of organic nonlinear optical materials having high hyperpolarizability and large dipole moments is limited by the tendency of these materials to aggregate when processed into electro-optic devices. The result is a loss of optical nonlinearity. The stability of these materials also limits their utility. Accordingly, there exist a need for improved nonlinear optically active materials having large hyperpolarizabilities, large dipole moments, and high stability and that, when employed in electro-optic devices, are stable and exhibit large electrooptic coefficients. The present invention seeks to fulfill these needs and provides further related advantages.

SUMMARY OF THE INVENTION

In one aspect, the invention provides pyrroline electron acceptor compounds. The electron acceptor compounds have utility in organic nonlinear optical applications. Methods for making the electron acceptor compounds are also provided.

In another aspect, the invention provides nonlinear optical chromophores that include a pyrroline electron acceptor group. Methods for making the nonlinear optical chromophores are also provided.

In a further aspect, the invention provides nonlinear optical chromophores that include a pyrrolizine electron acceptor group. Methods for making the nonlinear optical chromophores are also provided.

In other aspects, the invention provides lattices that include the nonlinear optical chromophores and devices that include the nonlinear optical chromophores are provided.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 8 compares some spectral properties for three pyrroline-containing chromophores;

FIG. 11 compares some spectral properties for three representative pyrroline-containing chromophores of the invention;

FIG. 12 is an illustration of the chemical structures of two pyrroline-containing representative chromophores of the invention;

FIG. 13 compares some physical, electro-optic, and spectral properties for three representative pyrroline-containing chromophores of the invention;

FIG. 14 is an illustration of the chemical structures of two representative families of pyrroline-containing chromophores of the invention;

FIG. 16 is an illustration of the chemical structures of four reprsentative pyrroline-containing chromophores of the invention;

FIG. 22 is an illustration of the chemical structures of four representative pyrrolizine-containing chromophores of the invention.

DETAILED DESCRIPTION OF THE PREFERRED EMBODIMENT

Figure 1:
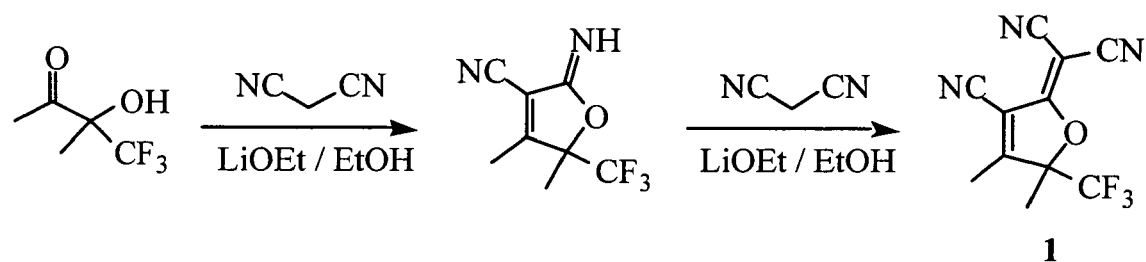
FIG. 1 is a schematic illustration of the preparation of 3-cyano-5-methyl-5-trifluoromethyl-2-dicyanomethylene-4-methyl-2,5-dihydrofuran, a prior art electron acceptor compound.

The present invention provides a new class of highly polarizable organic nonlinear optical (NLO) chromophores for optical waveguides and devices. In one embodiment, the chromophores include monocyano-, dicyano-, or tricyano-pyrroline electron acceptor groups with various electronic conjugation bridges and donor groups. In another embodiment, the chromophores include dicyano- or polycyano-pyrrolizine electron acceptor groups with various electronic conjugation bridges and donor groups. Polymeric composite thin films containing the chromophores can be used as active media in optical waveguides and devices such as electro-optical modulators, optical switches, optical sensors, and information processors.

Pyrroline Electron Acceptor Compounds

In one aspect, the invention provides pyrroline electron acceptor compounds. The electron acceptor compounds have utility in organic nonlinear optical (NLO) applications. The electron acceptor compounds exhibit high thermal and chemical stability.

The electron acceptor compounds can be used to make stable, nonlinear optical chromophores having large hyperpolarizabilities, large dipole moments, and that, when employed in electro-optic devices, exhibit large electro-optic coefficients. NLO chromophores made from the electron acceptor compounds of the invention include a pyrroline electron acceptor group (i.e., the portion of the chromophore derived from the electron acceptor compound). The electron acceptor group serves as an electron acceptor and further imparts advantageous properties to the chromophores. The chromophores of the invention are described below.

As used herein, the term "electron acceptor group" or "electron withdrawing group" refers to an electronegative organic substituent in a compound having a π-electron system that includes the electronegative organic substituent, where the electronegative organic substituent attracts electron density from the π-electron system when the compound is polarized by electromagnetic energy.

The term "electron acceptor compound" refers to a compound that is useful in making a nonlinear optical chromophore having an electron acceptor group, where the electron acceptor group is derived from the electron acceptor compound.

In one embodiment, the electron acceptor compounds of the invention are pyrroline electron acceptor compounds having formula (I):

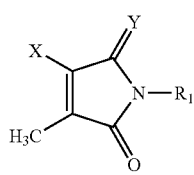

(I)

wherein X is hydrogen, fluorine, chlorine, bromine, cyano, substituted or unsubstituted alkyl (e.g., methyl), perfluoroalkyl (e.g., trifluoromethyl), substituted or unsubstituted aryl, ester (i.e., —C(═O)OR$_2$, where R$_2$ is substituted or unsubstituted alkyl, or substituted or unsubstituted aryl), amide (i.e., —C(═O)NR$_{2a}$R$_{2b}$, where R$_{2a}$ and R$_{2b}$ are independently hydrogen, substituted or unsubstituted alkyl, or substituted or unsubstituted aryl), alkyl or aryl sulfonyl (i.e., —SO$_2$R$_2$, where R$_2$ is substituted or unsubstituted alkyl, or substituted or unsubstituted aryl), or alkyl phosphonate (i.e., —P(═O)(OR$_{2a}$)(OR$_{2b}$), where R$_{2a}$ and R$_{2b}$ are independently hydrogen, substituted or unsubstituted alkyl, or substituted or unsubstituted aryl);

Y is O, S, NR$_3$, C(R$_{3a}$)(R$_{3b}$), Si(R$_{3a}$)(R$_{3b}$), or C(X$_a$)(X$_b$), where R$_3$ is hydrogen, substituted or unsubstituted alkyl, or substituted or unsubstituted aryl, where R$_{3a}$ and R$_{3b}$ are independently hydrogen, substituted or unsubstituted alkyl, or substituted or unsubstituted aryl, and where X$_a$ and X$_b$ are independently selected from X above; and R$_1$ is hydrogen, substituted or unsubstituted alkyl, substituted or unsubstituted aryl, or acyl (—C(═O)R$_2$, where R$_2$ is substituted or unsubstituted alkyl, or substituted or unsubstituted aryl).

In one embodiment, the electron acceptor compounds of the invention are tricyanopyrroline (TCP) electron acceptor compounds having formula (IA):

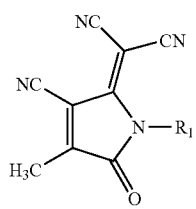

(IA)

wherein R$_1$ is hydrogen, substituted or unsubstituted alkyl, substituted or unsubstituted aryl, or acyl (—C(═O)R$_2$, where R$_2$ is substituted or unsubstituted alkyl, substituted or unsubstituted aryl).

In another embodiment, the electron acceptor compounds of the invention are dicyanopyrroline (DCP) electron acceptor compounds having formula (IIA), (IIB), or (IIC):

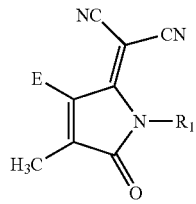

(IIA)

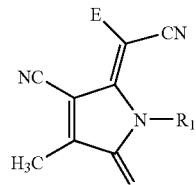

(IIB)

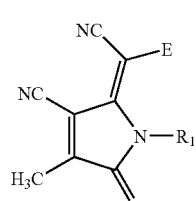

(IIC)

wherein R$_1$ is hydrogen, substituted or unsubstituted alkyl, substituted or unsubstituted aryl, or acyl (—C(═O) R$_2$, where R$_2$ is substituted or unsubstituted alkyl, substituted or unsubstituted aryl); and E is an ester group (e.g., —C(═O)OR$_2$, where R$_2$ is substituted or unsubstituted alkyl, substituted or unsubstituted aryl).

In another embodiment, the electron acceptor compounds of the invention are monocyanopyrroline (MCP) electron acceptor compounds having formula (IIIA), (IIIB), or (IIIC):

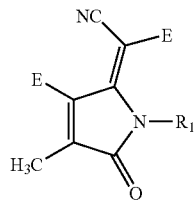

(IIA)

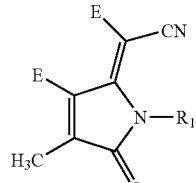

(IIB)

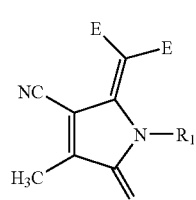

(IIC)

wherein R$_1$ is hydrogen, substituted or unsubstituted alkyl, substituted or unsubstituted aryl, or acyl (—C(═O)

$R_2$, where $R_2$ is substituted or unsubstituted alkyl, substituted or unsubstituted aryl); and E is an ester group (e.g., —C(=O)O$R_2$, where $R_2$ is substituted or unsubstituted alkyl, substituted or unsubstituted aryl).

Representative substituted and unsubstituted alkyl, and substituted and unsubstituted aryl groups ($R_1$ substituents) include —$C_nH_{2n+1}$; —$C_nH_{2n}OH$; —$C_nH_{2n}OCH_2OCH_3$; —$C_nH_{2n}OC_mH_{2m+1}$; —$C_nH_{2n}OSi(CH_3)_2(tBu)$; —$C_nH_{2n}OC(=O)C_mH_{2m+1}$; —$C_6H_4C_nH_{2n+1}$; —$C_6H_4OH$; —$C_6H_3(OH)_2$; —$C_6H_4SH$; —$C_6H_4OSi(CH_3)_2(tBu)$; —$C_6H_4NH_2$; —$C_6H_4CO_2H$; —$C_6H_4SO_3H$; —$C_6H_4PO_3H_2$; —$C_6H_4Si(OR)_3$; —$C_6F_5$; —$C_6F_4OH$; —$C_6F_4CO_2H$; —$C_6F_4N$; —$C_6F_4CF_3$; —$C_4H_3S$; —$C_4H_3O$; —$C_6H_3(OCF=CF_2)_2$; —$C_6H_3(OC_nH_{2n}C_6F_5)_2$; $C_{10}H_7C_nH_{2n+1}$; —$C_nH_{2n}CH=CH_2$; —$C_nH_{2n}CHOCHC_mH_{2m+1}$; —$C_nH_{2n}CO_2C_mH_{2m+1}$; —$C_nH_{2n}CO_2H$; —$C_nH_{2n}NH_2$; —$C_nH_{2n}Br$; —$C_nH_{2n}OSi(C_mH_{2m+1})_3$; —$C_nH_{2n}NC_2O_2C_2H_2$; —$C_nH_{2n}SO_3H$; —$C_nH_{2n}OCF=CF_2$; —$C_6H_4OR$; —C(=O)R; —$C_nH_{2n}C(=O)R$; and —$C_nH_{2n}R$; where R is substituted or unsubstituted alkyl, or substituted or unsubstituted aryl, where n=1-10, and m=1-10.

As used herein, the term "alkyl" refers to a saturated or unsaturated, straight or branched, cyclic or multicyclic aliphatic (i.e., non-aromatic) hydrocarbon group containing from 1 to about 30 carbons. Independently the hydrocarbon group, in various embodiments: has zero branches (i.e., is a straight chain), one branch, two branches, or more than two branches; is saturated; is unsaturated (where an unsaturated alkyl group may have one double bond, two double bonds, more than two double bonds, and/or one triple bond, two triple bonds, or more than three triple bonds); is, or includes, a cyclic structure; is acyclic. Exemplary alkyl groups include $C_1$alkyl (i.e., —$CH_3$ (methyl)), $C_2$alkyl (i.e., —$CH_2CH_3$ (ethyl), —CH=$CH_2$ (ethenyl) and —C≡CH (ethynyl)) and $C_3$alkyl (i.e., —$CH_2CH_2CH_3$ (n-propyl), —$CH(CH_3)_2$ (I-propyl), —CH=CH—$CH_3$ (1-propenyl), —C≡C—$CH_3$ (1-propynyl), —$CH_2$—CH=$CH_2$ (2-propenyl), —$CH_2$—C≡CH (2-propynyl), —C($CH_3$)=$CH_2$ (1-methylethenyl), —$CH(CH_2)_2$ (cyclopropyl), and adamantly. The term "alkyl" also includes groups where at least one of the hydrogens of the hydrocarbon group is substituted with at least one of the following: alkyl; "aryl" as defined below; or "heteroalkyl" as defined below. One or more of the atoms in an alkyl group, with the exception of hydrogen, can be bonded to one or more of the atoms in an adjacent alkyl group, aryl group (aryl as defined below), or heteroalkyl group (heteroalkyl as defined below) to form one or more ring.

Representative substituted alkyl groups include the following groups: —$C_nH_{2n}OH$; —$C_nH_{2n}OCH_2OCH_3$; —$C_nH_{2n}OC_mH_{2m+1}$; —$C_nH_{2n}OSi(CH_3)_2(tBu)$; and —$C_nH_{2n}OC(=O)C_mH_{2m+1}$; where n=1-10 and m=1-10.

The term "aryl" refers to a monocyclic or polycyclic aromatic ring system or a heteroaromatic ring system containing from 3 to about 30 carbons. The ring system may be monocylic or fused polycyclic (e.g., bicyclic, tricyclic, etc.). Preferred heteroatoms are nitrogen, oxygen, sulfur, and boron. In various embodiments, the monocyclic aryl ring is C5-C10, or C5-C7, or C5-C6, where these carbon numbers refer to the number of carbon atoms that form the ring system. A C6 ring system, i.e., a phenyl ring, is a preferred aryl group. A C4-S ring system (i.e., a thiophene) is another preferred aryl group. A C4-O ring system (i.e., a furan) is another preferred aryl group. In various embodiments, the polycyclic ring is a bicyclic aryl group, where preferred bicyclic aryl groups are C8-C12, or C9-C10. A naphthyl ring, which has 10 carbon atoms, is a preferred polycyclic group. The term "aryl" also includes groups where at least one of the hydrogens of the aromatic or heteroaromatic ring system is substituted further with at least one of the following: alkyl; halogen; or heteroalkyl (as defined below). One or more of the atoms in an aryl group, with the exception of hydrogen, can be bonded to one or more of the atoms in an adjacent alkyl group, aryl group, or heteroalkyl group (heteroalkyl as defined below) to form one or more rings.

Representative substituted aryl groups include —$C_6H_4C_nH_{2n+1}$; —$C_6H_4OH$; —$C_6H_3(OH)_2$; —$C_6H_4SH$; —$C_6H_4OSi(CH_3)_2(tBu)$; —$C_6H_4NH_2$; —$C_6H_4CO_2H$; —$C_6H_4SO_3H$; —$C_6H_4PO_3H_2$; —$C_6H_4Si(OR)_3$, where R is substituted or unsubstituted alkyl, or substituted or unsubstituted aryl; —$C_6F_5$; —$C_6F_4OH$; —$C_6F_4CO_2H$; —$C_6F_4N$; —$C_6F_4CF_3$; —$C_4H_3S$; —$C_4H_3O$; —$C_6H_3(OCF=CF_2)_2$; —$C_6H_3(OC_nH_{2n}C_6F_5)_2$; and $C_{10}H_7C_nH_{2n+1}$; where n=1-10.

The term "heteroalkyl" refers to an alkyl group (as defined herein) wherein at least one of carbon atoms or hydrogen atoms is replaced with a heteroatom, with the proviso that at least one carbon atom must remain in the heteroalkyl group after the replacement of carbon or hydrogen with a heteroatom. Preferred heteroatoms are nitrogen, oxygen, sulfur, silicon, and halogen. A heteroatom may, but typically does not, have the same number of valence sites as the carbon or hydrogen atom it replaces. Accordingly, when a carbon is replaced with a heteroatom, the number of hydrogens bonded to the heteroatom may need to be increased or decreased to match the number of valence sites of the heteroatom. For instance, if carbon (valence of four) is replaced with nitrogen (valence of three), then one of the hydrogens formerly attached to the replaced carbon must be deleted. Likewise, if carbon is replaced with halogen (valence of one), then three (i.e., all) of the hydrogens formerly bonded to the replaced carbon must be deleted. Examples of heteroalkyls derived from alkyls by replacement of carbon or hydrogen with heteroatoms is shown immediately below. Exemplary heteroalkyl groups are methoxy (—$OCH_3$), amines (—$CH_2NH_2$), nitriles (—CN), carboxylic acids (—$CO_2H$), other functional groups, and dendrons. The term "heteroalkyl" also includes groups where at least one of the hydrogens of carbon or a heteroatom of the heteroalkyl may be substituted with at least one of the following: alkyl; aryl; and heteroalkyl. One or more of the atoms in a heteroalkyl group, with the exception of hydrogen, can be bonded to one or more of the atoms in an adjacent alkyl group, aryl group, or heteroalkyl group to form one or more rings.

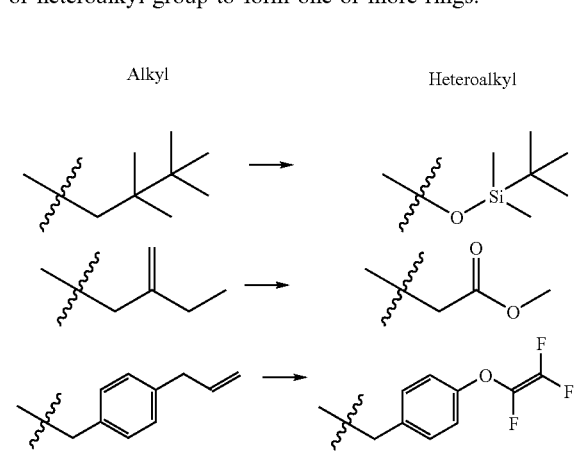

Alkyl          Heteroalkyl

-continued

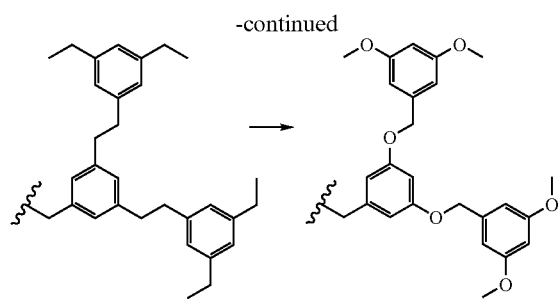

The substituent list that follows is not meant to limit the scope of the definitions above or the inventions described below, but rather merely contains examples of substituents within the definitions above: (1) (alkyl)-$CH_3$; —i-Pr, —n-Bu, —t-Bu, —i-Bu, —$CH_2CH=CH_2$ (allyl) —$CH_2C_6H_5$ (benzyl); (2) (heteroalkyl) —$X_{(0-1)}(CH_2)_{(0-12)}(CF_2)_{(0-12)}$ $(CH_2)_{(0-12)}CH_pZ_q$ (where X includes —O, —S, —$CO_2$— (ester), Z=halogen, p=0-3, q=0-3, and p+q=3) and branched isomers thereof, —$X_{(0-1)}(CH_2)_{(0-12)}(CF_2)_{(0-12)}(CH_2)_{(0-12)}Z$ (where X includes —O, —S, —$CO_2$— (ester), Z includes —OH, —$NH_2$, —$CO_2H$ and esters and amides thereof, —COCl, and —NCO) and branched isomers thereof, —$OCFCF_2$ (TFVE), —$Si(CH_3)_3$ (TMS), —$Si(CH_3)_2$(t-Bu) (TBDMS),—$Si(C_6H_5)$ (TPS), —$Si(C_6F_5)_3$, and dendrons such as illustrated in the dendrimers discussed in Bosman, et al., Chem. Rev. 99:1665-1688, 1957; (3) (aryl) —$C_6H_5$ (phenyl), p-, o-, and/or m-substituted phenyl (with substituents independently selected from —$CH_3$, —i-Pr, —n-Bu, —t-Bu, —i-Bu, —$X_{(0-1)}(CH_2)_{(0-12)}(CF_2)_{(0-12)}(CH_2)_{(0-12)}$ $CH_pZ_q$ (where X includes —O, —S, —$CO_2$-(ester), Z=halogen, p=0-3, q=0-3, and p+q=3) and branched isomers thereof, —$X_{(0-1)}(CH_2)_{(0-12)}(CF_2)_{(0-12)}(CH_2)_{(0-12)}Z$ (where X includes, —O, —S, —$CO_2$— (ester), Z includes —OH, —$NH_2$, —$CO_2H$ and esters and amides thereof, —TFVE, —COCl, and —NCO) and branched isomers thereof, —Si$(CH_)_3$ (TMS), —$Si(CH_3)_2$(t-Bu) (TBDMS), —$CH_2CH=CH_2$ (allyl), and TFVE) and dendrons as illustrated in the dendrimers discussed in Bosman, et al., Chem. Rev. 99:1665, 1999 or U.S. Pat. No. 5,041,516.

Figure 2:
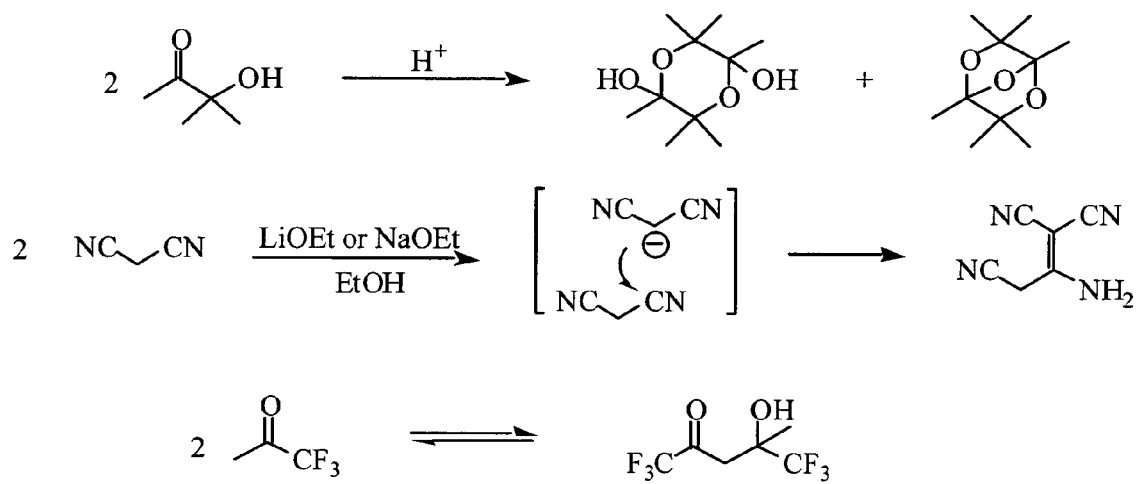
FIG. 2 is a schematic illustration of the side reactions encounter in the preparation of 3-cyano-5-methyl-5-trifluoromethyl-2-dicyanomethylene-4-methyl-2,5-dihydrofuran: the dimerization of 3-methyl-3-hydroxy-2-butanone; the dimerization of malononitrile; and the cyclization of 1,3-bis(trifluoromethyl)-3-hydroxy-2-butanone.

Syntheses of the pyrroline electron acceptor compounds of the invention is described below in relation to previously synthesized electron acceptor compounds. The synthesis of the trifluoromethyl substituted tricyanofuran (TCF) acceptor 1, shown in FIG. 1, is problematic due to the dimerization of starting ketols, the dimerization of malononitrile, and the dimerization of trifluoroacetone, as shown in FIG. 2. The trifluoromethyl substituted TCF acceptor ($CF_3$-TCF, 3-cyano-5-methyl-5-trifluoromethyl-2-dicyanomethylene-4-methyl-2,5-dihydrofuran) can be synthesized more efficiently using microwave radiation as heating source than conventional heating. The rate of Pinnar type intramolecular cyclization increase significantly than the rate of dimerization of malononitrile via microwave radiation. The dimer of the malonitrile is known to be a main by-product in more conventional one-pot reaction in refluxing ethanol.

Figure 3:
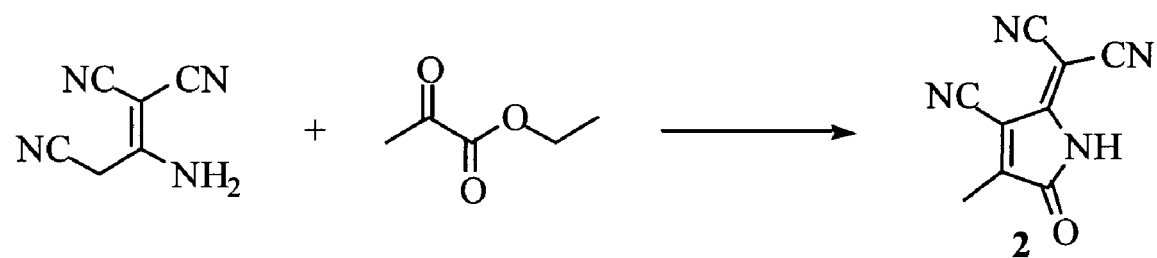
FIG. 3 is a schematic illustration of the preparation of a representative electron acceptor compound of the invention, 4-cyano-3-methyl-5-dicyanomethylene-2-oxo-3-pyrroline.

The understanding of the dimerizations of malononitrile and trifluoroacetone, and finding the optimized reaction condition for the acceptor 1 led to the discovery of several ways to design and synthesize a series of very efficient tricyano pyrrolinone (TCP) acceptors and TCP chromophores using combinatorial acceptor design strategy as shown below in the case of a reaction between malononitrile dimer and ethyl pyruvate resulting TCP acceptor 2, a representative pyrroline electron acceptor compound of the invention, as shown in FIG. 3.

Experiments with the $CF_3$-TCF showed that trifluoromethyl substitution of a spiro methyl group in the TCF chromorphores results in a dramatic red shift in absorption maxima in various solvents. To understand the nature of charge transfer band and interactions of HOMO and LUMO of the chromophores, a series of molecular orbital calculations on related model chromophores was performed. From a series of calculations of model components, it was determined that the cause of the red shift in trifluoromethyl substituted chromophores is a result of the induction effect of trifluoromethyl groups in the HOMO and the resonance contribution of trifluoromethyl group in the LUMO.

Figure 4:
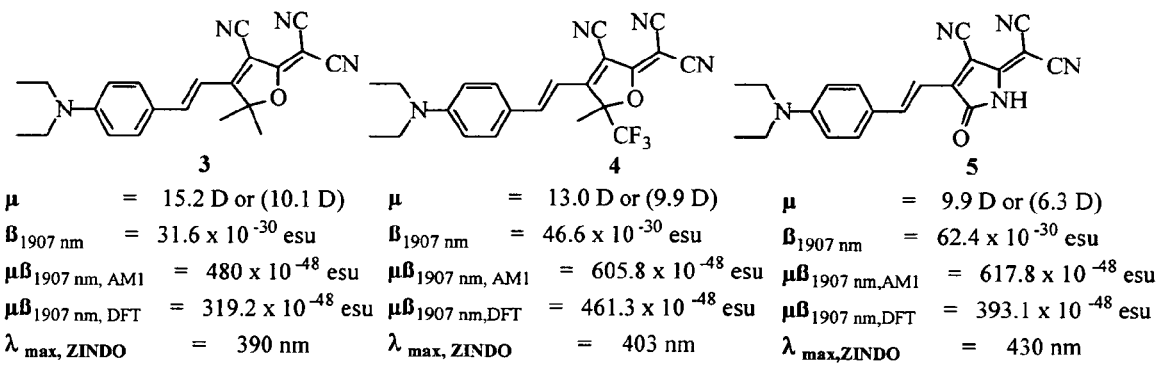
FIG. 4 compares some physical, electro-optic, and spectral properties for three pyrroline-containing chromophores.

The calculated hyperpolarizabilities along with absorption maxima of electronic transitions for simple diethylamino-styryl-TCP model chromophores using the INDO/S-CI method on AM1 ground state conformations showed systematic improvement in linear and nonlinear optical polarizabilities in the order of TCF chromophores 3 less than $CF_3$-TCF chromophore 4 less than TCP chromophore 5. Chromophores 3-5 and the calculated results are illustrated in FIG. 4.

The pyrroline-based chromophores of the invention (e.g., chromophore 5) differ from model chromophores (e.g., chromophores 3 and 4) in that the chromophores of the invention include a carbonyl group rather than a spiro bis-dialkyl group adjacent the dihydrofuran oxygen. The chromophore's HOMO gives a major contribution in ground state dipole moment affecting transition dipole moment significantly. Comparing the frontier orbitals for these chromophores, it was found that the carbonyl substituted TCP acceptors gave significantly enhanced hyperpolarizabilities (μβ) (see FIG. 4) compared to TCF and $CF_3$-TCF chromophores. No noticeable orbital coefficients are apparent on the nitrogen atom in the HOMO and LUMO of TCP chromophore 5.

One advantage of the pyrroline electron acceptor compounds of the invention and chromophores that include the pyrroline electron groups is the flexibility for chemical modifications to tune required chemical and optical properties of the chromophores. Depending on the combination of donor bridges and acceptor group used, it is possible to build a library of related chromophores systematically.

The electron acceptor compounds of the invention can be prepared by reacting an appropriately substituted imine compound with an appropriately substituted methylene compound using microwave irradiation as described in WO 2004/065384, incorporated herein by reference in its entirety.

Figure 7:
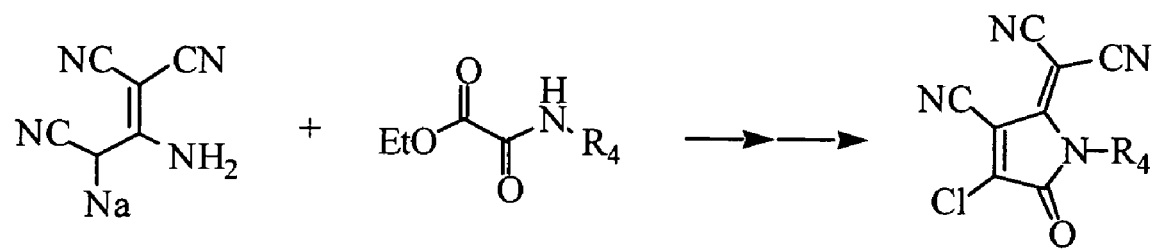
FIG. 7 is a schematic illustration of a method for preparing a representative pyrroline electron acceptor compound of the invention.

The preparation of representative electron acceptor compounds of the invention are illustrated in FIGS. 3 and 7. The preparation of a representative electron acceptor compound of the invention is described in Example 1.

Chromophores Containing Pyrroline and Pyrrolizine Electron Acceptor Groups

In another aspect, the present invention provides NLO chromophores that are useful in electro-optic devices. In one embodiment, the NOL chromophores include a pyrroline electron acceptor group. In another embodiment, the NLO chromophores include a pyrrolizine electron acceptor group.

As used herein, the term "chromophore" refers to a compound or moiety that can absorb a photon of light. In the context of the chromophores of the invention, the term "nonlinear" refers second order effects that arise from the nature of the polarizable chromophore (i.e., "push-pull" chromophore moieties) having the general structure D-$\pi_a$-

B-$\pi_b$-A, where D is an electron donor group, A is an electron acceptor group, B is a conjugated bridge group, $\pi_a$ is a π-bridge group that conjugates the donor group to the bridge group, $\pi_b$ is a π-bridge group that conjugates the bridge group to the acceptor group. In the chromophores of the invention, each of $\pi_a$ and $\pi_b$ is optional. When $\pi_a$ is absent, the chromophores of the invention have the general structure D-B-$\pi_b$-A; when $\pi_b$ is absent, the chromophores of the invention have the general structure D-$\pi_a$-B-A; and when $\pi_a$ and $\pi_b$ are absent, the chromophores of the invention have the general structure D-B-A. With or without π-bridge groups $\pi_a$ and $\pi_b$, the chromophore's electron donor group is electronically conjugated to the electron acceptor group through the bridge group.

An "electron donor group" or "donor" (represented by "D") is an atom or group of atoms with low electron affinity relative to an electron acceptor group (defined below) such that, when the donor group is conjugated to an acceptor group through a bridge group, electron density is transferred from the donor group to the acceptor group.

An "electron acceptor group" or "acceptor" (represented by "A") is an atom or group of atoms with high electron affinity relative to a donor group such that, when the acceptor group is conjugated to a donor group through a bridge group, electron density is transferred from the acceptor group to the donor group. The chromophores of the invention have either a pyrroline or a pyrrolizine electron acceptor group.

A "bridge group" or "conjugated bridge" (represented in chemical structures by "B") is comprised of an atom or group of atoms through which electrons can be delocalized from an electron donor group to an electron acceptor group through the orbitals of atoms in the bridge. Preferably, the orbitals will be p-orbitals on multiply bonded carbon atoms such as those found in alkenes, alkynes, neutral or charged aromatic rings, and neutral or charged heteroaromatic ring systems. Additionally, the orbitals can be p-orbitals on multiply bonded arms such as boron or nitrogen or organometallic orbitals. The atoms of the bridge group that contain the orbitals through which the electrons are delocalized are referred to here as the "critical atoms." The number of critical atoms in a bridge group can be a number from 1 to about 30. The critical atoms can also be substituted further with the alkyl, aryl, or heteroalkyl groups, as defined herein. One or more atoms, with the exception of hydrogen, on alkyl, aryl, or heteroalkyl substituents of critical atoms in the bridge group may be bonded to atoms in other alkyl, aryl, or heteroalkyl substituents to form one or more rings.

The groups "$\pi_a$" and "$\pi_b$" provide electronic conjugation between the electron donor and bridge group, and between the bridge and electron acceptor group, respectively. Each of groups "$\pi_a$" and "$\pi_b$" is comprised of an atom or group of atoms through which the electrons can be delocalized from an electron donor group to an electron acceptor group through the bridge. Preferably, the orbitals will be p-orbitals on multiply bonded carbon atoms such as those found in alkenes, alkynes, neutral or charged aromatic rings, and neutral or charged heteroaromatic ring systems. In a particular chromophore, groups "$\pi_a$" and "$\pi_b$" need not be the same. Representative groups "$\pi_a$" and "$\pi_b$" include ethylene (—CH=CH—), butylene (—CH=CH—CH=CH—), and hexylene (—CH=CH—CH=CH—CH=CH—) groups. In these groups, the hydrogen atoms may be substituted as described above for the bridge group.

Representative pyrroline-containing chromophores of the invention are illustrated in FIGS. 5, 6, 9-16, 18, and 23. The preparations of representative pyrroline-containing chromophores of the invention are described in Examples 2-9. Representative pyrrolizine-containing chromophores of the invention are illustrated in FIGS. 19-22.

The chromophores of the invention are characterized as having high electro-optic coefficients; large hyperpolarizability; large dipole moments; chemical, thermal, electrochemical, and photochemical stability; low absorption at operating wavelengths (e.g., 1.3 and 1.55 μm); suitable solubility in spin casting solvents; compatibility with polymer hosts; and low volatility.

Optical Hyperpolarizability (μβ). Nonlinear optical effects of organic materials depend mainly on the compound's hyperpolarizability (β). A measure of organic chromophore nonlinearity is μβ, where μ is the chromophore dipole moment. A chromophore's optical nonlinearity (μβ) can be measured as described in Dalton et al., "Impotence of Intermolecular Interactions in the Nonlinear Optical Properties of Poled Polymers", *Applied Physics Letters,* Vol. 76, No. 11, pp. 1368-1370 (2000).

The chromophores of the invention are characterized as having high optical nonlinearities. In certain embodiments, the invention provides chromophores having optical nonlinearities with μβ or greater than about $10,000 \times 10^{-48}$ esu. In other embodiments, chromophores are provided having optical nonlinearities with μβ up to at least about $5,000 \times 10^{-69}$ in $Cm^5/V$ measured at 1907 nm.

Electro-Optic Coefficient ($r_{33}$). A chromophore's electro-optic coefficient ($r_{33}$) can be measured in a polymer matrix using attenuated total reflection (ATR) technique at telecommunication wavelengths of 1.3 or 1.55 μm. A representative method for measuring the electro-optic coefficient is described in Dalton et al., "Importance of Intermolecular Interactions in the Nonlinear Optical Properties of Poled Polymers", *Applied Physics Letters,* Vol. 76, No. 11, pp. 1368-1370 (2000).

Representative pyrroline acceptor-containing chromophores (e.g., TCP chromophores) were synthesized to study and optimize their chemical and optical properties for various photonics applications. UV-vis spectral data in relation to calculated electronic spectra was studied to understand and compare the trends in charge transfer absorption band. Solvatochromism of several model TCP chromophores were measured to understand and compare their hyperpolarizabilities with reported TCF chromophores and other model chromophores. These measurements can be used to determine hyperpolarizabilities of chromophores for a qualitive comparison within a closely related series of chromophores. Representative TCP chromophores show very strong solvatochromism comparable to best known TCF chromophores with significantly shorter conjugation lengths. Structures and spectral data for some model TCF chromophores (3 and 4) and representative TCP chromophores (5-14) chromophores are shown with solvatochromism data for comparison in FIGS. 8-11.

Figure 10:
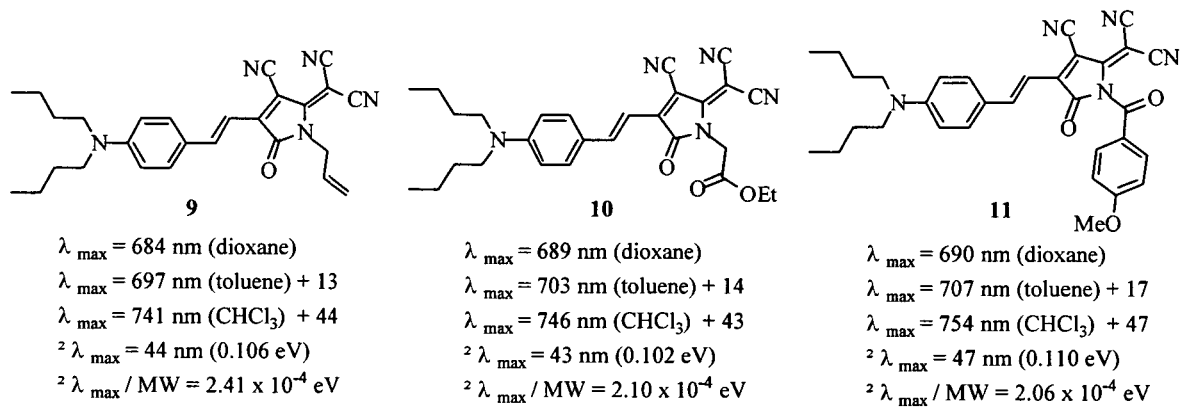
FIG. 10 compares some spectral properties for three representative pyrroline-containing chromophores of the invention.

Linear and nonlinear optical properties of the TCP chromophore can be turned by modifications of electronic donor, bridge, and acceptor structures. As shown in FIG. 10, modification of representative TCP chromophore 5 with substitution of NH proton with allyl group gives red shift of 8 nm in absorption maxima (chromophore 9), 13 nm with substitution with methylene ester (chromophore 10), and 14 nm with substitution with acyl group (chromophore 11) in dioxane. The substituents in donor bridges affect the optical properties more significantly. Exo-ester group substitutions in the bis-ethanolamino phenyl donor in representative TCP chromophore 5 show impressive blue shifts of 41 nm (from 676 nm to 635 nm) in dioxane and 63 nm (from 738 nm to 675) (chromophore 7) in chloroform in absorption maxima with a single double bond between donor and acceptor. Trimethyl-bis-dimethylsilane (TBDMS) protection of the bis-ethanol amino phenyl donor provides chromophore 8 which exhibits blue shifts of 13 nm (from 676 nm to 663 nm) in dioxane and 17 nm (from 738 nm to 721 nm) in chloroform.

Structural modifications on donor bridges of representative chromophores 7 and 8 were designed to demonstrate the incorporation of these chromophores into a chemically linked side chain polymeric composites. Substituents in chromophores 9 and 10 can be used as crosslinkers. Thus, multiple sites for crosslinking and the chemical incorporation of these chromophores into polymeric composites are available though the chromophores of the invention.

The electro-optic properties of two representative chromophores of the invention chromophores 11 and 15 (see FIG. 12) was determined. The EO activity ($r_{33}$) measurement of representative chromophore 11 doped in amorphous polycarbonate (APC) matrix as guest/host system showed an impressive 18 pm/V with 10 wt % loading density when poled with 100 V/μm at 1.3 μm. Chromophore 15 doped in APC film as guest/host system shows an extremely high $r_{33}$ value: 51 pm/V with 20 wt % loading density when poled with 65 V/μm at 1.5 μm.

The thermal properties of representative chromophores was studied using isothermal heating and DSC experiments. Representative chromophore 9 (95%) was significantly more thermo-chemically robust than TCF (80%) and $CF_3$-TCF (48%) chromophores in PQ-100 matrix at 170° C.

In addition to the above-mentioned flexibilities, chromophore acceptor strength can be tuned and optimized by the proper substitution of the acceptor group's cyano group with less electron-withdrawing groups, such as the ester group. Model calculations showed that the efficiency-transparency trade-off can be optimized by choice of the substitution shown in FIG. 13. Derivatives of dicyano pyrroline (DCP) and monocyano pyrroline (MCP) acceptors were prepared by using appropriate malononitrile dimer derivatives, rather than the malononitrile dimer, in the reaction with ethyl pyruvate (see FIG. 3).

Representative pyrroline-containing chromophores of the invention have formulas (IV) and (V):

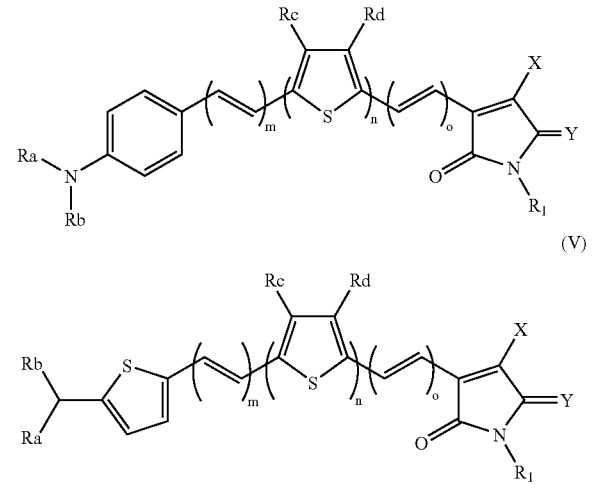

wherein m=0, 1, or 2; n=0, 1, 2, 3, 4, 5, or 6; and o=0, 1, or 2; and for chromophores having formula (IV) where X is CN and Y is $C(CN)_2$, in one embodiment at least one of m, n, or o is $\geq 1$, and in another embodiment when m=1 or 2, n is $\leq 1$;

wherein Ra, Rb, Rc, and Rd are independently selected from hydrogen, substituted or unsubstituted alkyl, and substituted and unsubstituted aryl, wherein X is hydrogen, fluorine, chlorine, bromine, cyano, substituted or unsubstituted alkyl (e.g., methyl), perfluoroalkyl (e.g., trifluoromethyl), substituted or unsubstituted aryl, ester (i.e., —C(=O)OR$_2$, where R$_2$ is substituted or unsubstituted alkyl, or substituted or unsubstituted aryl), amide (i.e., —C(=O)NR$_{2a}$R$_{2b}$, where R$_{2a}$ and R$_{2b}$ are independently hydrogen, substituted or unsubstituted alkyl, or substituted or unsubstituted aryl), alkyl or aryl sulfonyl (i.e., —SO$_2$R$_2$, where R$_2$ is substituted or unsubstituted alkyl, or substituted or unsubstituted aryl), or alkyl phosphonate (i.e., —P(=O)(OR$_{2a}$)(OR$_{2b}$), where R$_{2a}$ and R$_{2b}$ are independently hydrogen, substituted or unsubstituted alkyl, or substituted or unsubstituted aryl);

wherein Y is O, S, NR$_3$, C(R$_{3a}$)(R$_{3b}$), Si(R$_{3a}$)(R$_{3b}$), or C(X$_a$)(X$_b$), where R$_3$ is hydrogen, substituted or unsubstituted alkyl, or substituted or unsubstituted aryl, where R$_{3a}$ and R$_{3b}$ are independently hydrogen, substituted or unsubstituted alkyl, or substituted or unsubstituted aryl, and where X$_a$ and X$_b$ are independently selected from X above; and wherein R$_1$ is hydrogen, substituted or unsubstituted alkyl, substituted or unsubstituted aryl, or acyl (—C(=O)R$_2$, where R$_2$ is substituted or unsubstituted alkyl, or substituted or unsubstituted aryl).

Representative pyrrolizine-containing chromophores of the invention have formulas (VI) and (VII):

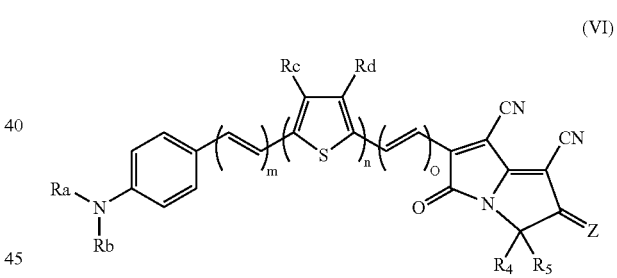

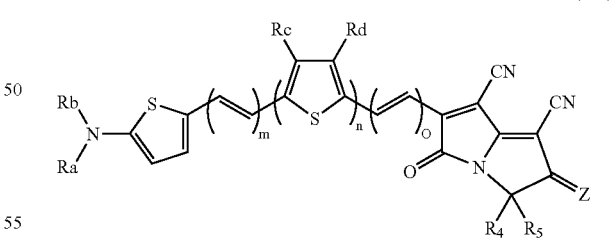

wherein m=0, 1, or 2; n=0, 1, 2, 3, 4, 5, or 6; and o=0, 1, or 2;

wherein Ra, Rb, Rc, and Rd are independently selected from hydrogen, substituted or unsubstituted alkyl, and substituted and unsubstituted aryl, wherein Z is O, S, NR$_3$, C(CN)$_2$, C(CN)(COR$_{3a}$), or C(CN)(CO$_2$R$_{3a}$), where R$_3$ is hydrogen, substituted or unsubstituted alkyl, or substituted or unsubstituted aryl, and where R$_{3a}$ is substituted or unsubstituted alkyl, or substituted or unsubstituted aryl; and wherein $R_4$ and $R_5$ are independently selected from hydrogen, substituted or unsubstituted alkyl, or substituted or unsubstituted aryl.

For the chromophores of the invention, representative substituted and unsubstituted alkyl groups, substituted and unsubstituted aryl groups, and acyl groups are as described above for the electron acceptor compounds.

In another aspect, the present invention provides methods for making NLO chromophores. In one embodiment, the invention provides a method for making a chromophore that includes a pyrroline electron acceptor group. In another embodiment, the invention provides a method for making a chromophore that includes a pyrrolizine electron acceptor group.

Figure 5:
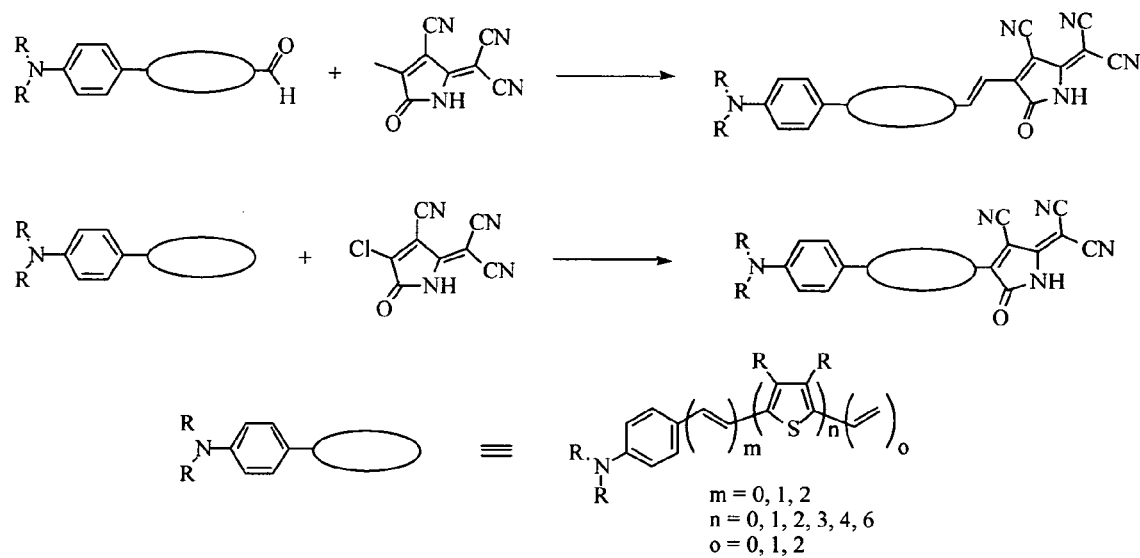
FIG. 5 is a schematic illustration of two methods for preparing representative pyrroline-containing chromophores of the invention.

The invention provides three general synthetic strategies for preparing chromophores that include pyrroline electron acceptor groups: (1) the condensation of a donor-bridge compound and a pyrroline electron acceptor compound; (2) the condensation of a donor-bridge compound and a pyrroline electron acceptor compound (e.g., TCP acceptor, 4-cyano-3-methyl-5-dicyanomethylene-2-oxo-3-pyrroline) generated in situ as one pot reaction, and (3) the nucleophilic substitution of a donor-bridge compound with a pyrroline electron acceptor compound (e.g., TCP chloride acceptor, 3-chloro-4-cyano-5-dicyanomethylene-2-oxo-3-pyrroline). FIG. 5 schematically illustrates the preparation of representative chromophores of the invention noted above. In FIG. 5, generic chemical structures for donor-bridge compounds (including electron donor and conjugation bridge) are shown with short cut notation. In addition to the short cut notation, FIG. 5 also illustrates the chemical structures of a family donor-bridge compounds useful in making representative chromophores of the invention. The ability to tune the chemical, optic, and electro-optic properties of chromophores as provided by the compounds, chromophores, and methods of the invention are important in designing materials for practical applications not only for the purpose of incorporating the chromophores in a polymer matrix, but for the optimization of properties and structures of bulk materials.

Figure 15:
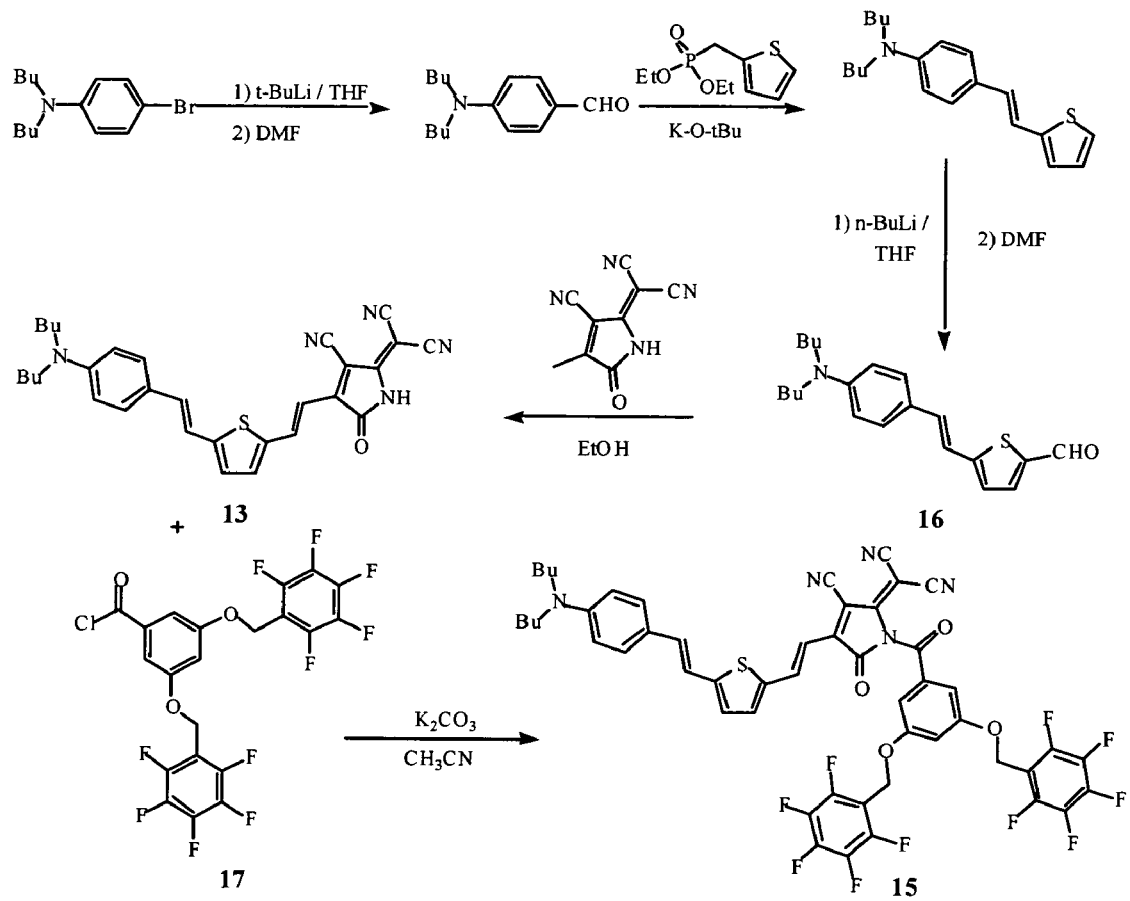
FIG. 15 is a schematic illustration of the preparation of representative pyrroline-containing chromophores of the invention.

In one embodiment, NLO chromophores of the invention (e.g., D-π-B-π-A) are made by reacting an electron acceptor compound of the invention (e.g., compounds having formulas I-IIIC above) with a donor-bridge compound having an aldehyde functionality (e.g., D-π-B-CHO) that is reactive toward coupling with the acceptor compound. The reaction of an electron acceptor compound of the invention with a donor-bridge compound having suitably reactive aldehyde functionality to provide an NLO chromophore is illustrated in FIGS. 5 and 15.

In one embodiment, NLO chromophores of the invention are prepared by reacting an appropriately substituted acceptor compound with appropriately substituted donor-bridge compound using focused microwave irradiation, as described in WO 2004/065384, incorporated herein by reference in its entirety.

In another embodiment, NLO chromophores of the invention (e.g., D-π-B-π-A) are made by reacting a suitably substituted pyrroline electron acceptor compound (e.g., a halo-TCP acceptor, such as 3-chloro-4-cyano-5-dicyanomethylene-2-oxo-3-pyrroline) with a suitably reactive donor-bridge compound. The reaction of a pyrroline electron acceptor compound with a donor-bridge compound having suitably reactive functionality to provide an NLO chromophore is illustrated in FIG. 5.

Figure 6:
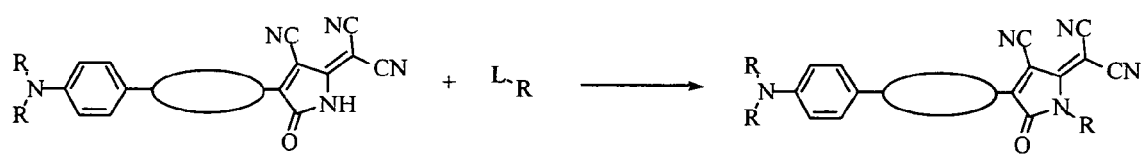
FIG. 6 is a schematic illustration of a method for preparing representative N-substituted pyrroline-containing chromophores of the invention.

Various chemical modification of donor, conjugation bridge, and acceptor structures can be made to tune the hyperpolarizability, dipole-dipole interactions, thermochemical, photochemical, and optical properties. The pyrroline acceptor compounds and pyrroline acceptor-containing chromophores include a terminal NH group that can be further derivatized to provide another chromophore. The chemical modification of a representative chromophore of the invention to provide an N-substituted chromophore is illustrated schematically in FIG. 6. Referring to FIG. 6, a representative pyrroline accepto-containing chromophore is further reacted by, for example, nucleophilic alkylation or acylation with various common alkyl halides (L-R) using known procedures. Such further derivatization can provide chromophores having functionalizable crosslinkers for the incorporation of chromophores into polymers, dendrimers, and other substrates.

Alternatively, N-substituted pyrroline acceptor-containing chromophores can be prepared from N-substituted pyrroline acceptor compounds, For example, 3-chloro-4-cyano-5-dicyanomethylene-2-oxo-3-pyrroline with alkyl, acyl, or aromatic substitution can be prepared by reaction of substituted malononitrile dimer and ethyl oxalate as illustrated in FIG. 7. N-Substituted pyrroline acceptor compounds prepared as illustrated in FIG. 7 can be reacted with donor-bridge compounds as illustrated in FIG. 5 to provide chromophores of the invention.

Figure 19:
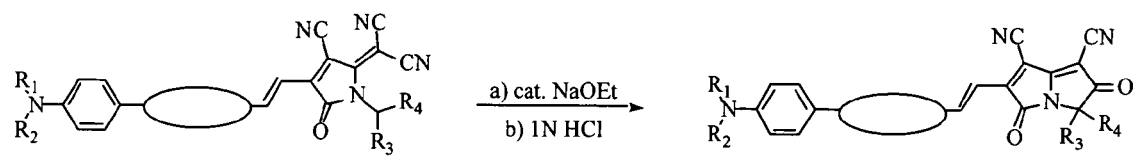
FIG. 19 is a schematic illustration of a method for preparing representative pyrroline-containing chromophores of the invention.
Figure 20:
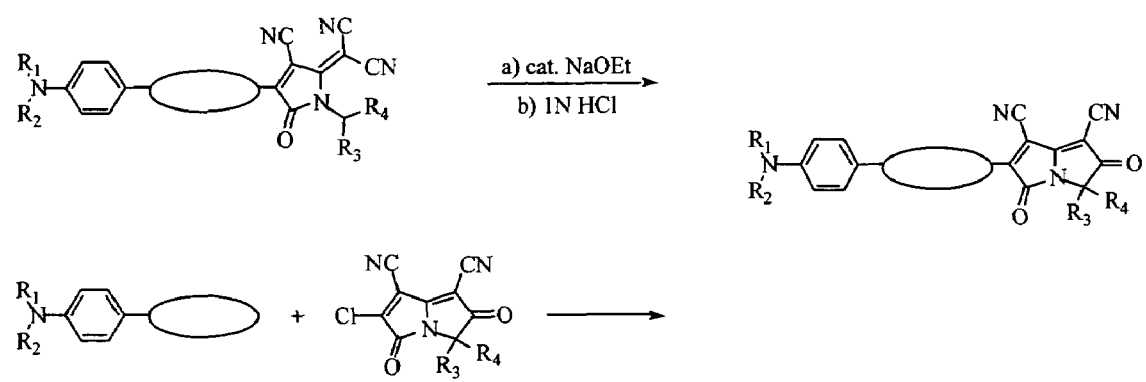
FIG. 20 is a schematic illustration of two methods for preparing representative pyrrolizine-containing chromophores of the invention.
Figure 21:
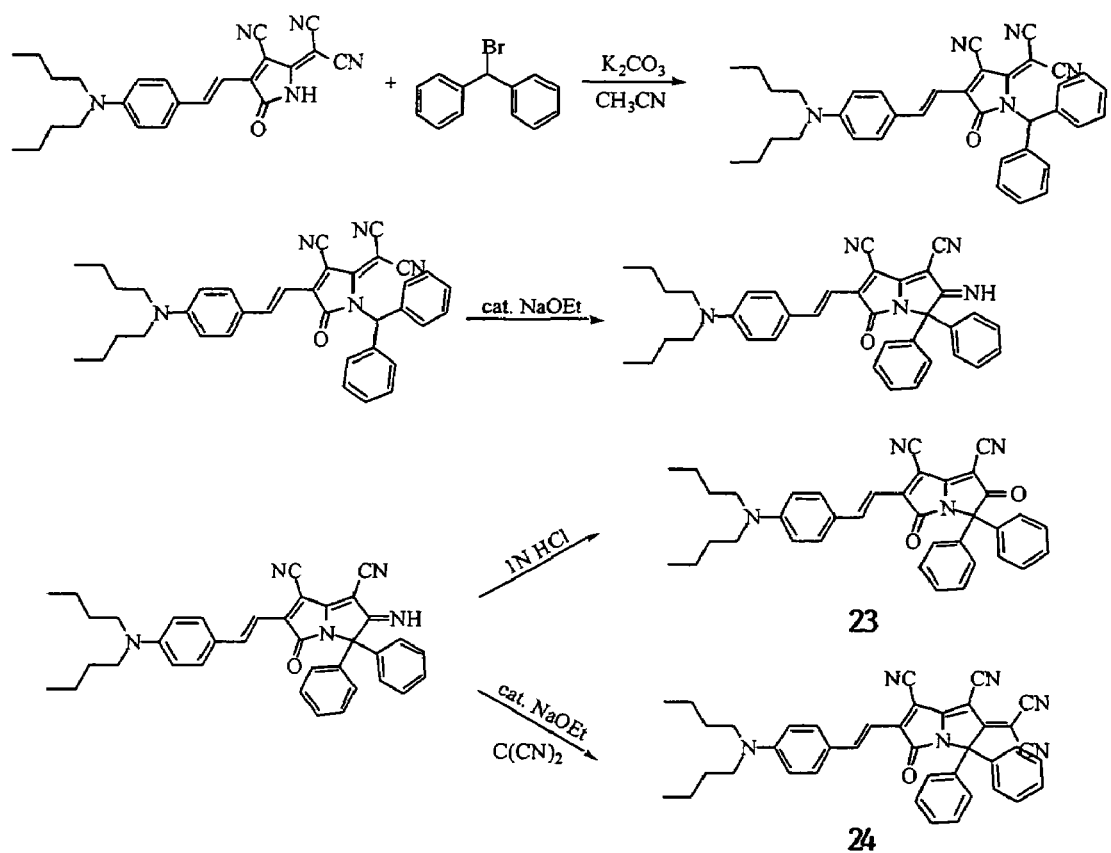
FIG. 21 is a schematic illustration of a method for preparing three representative pyrrolizine-containing chromophores of the invention.
Figure 23:
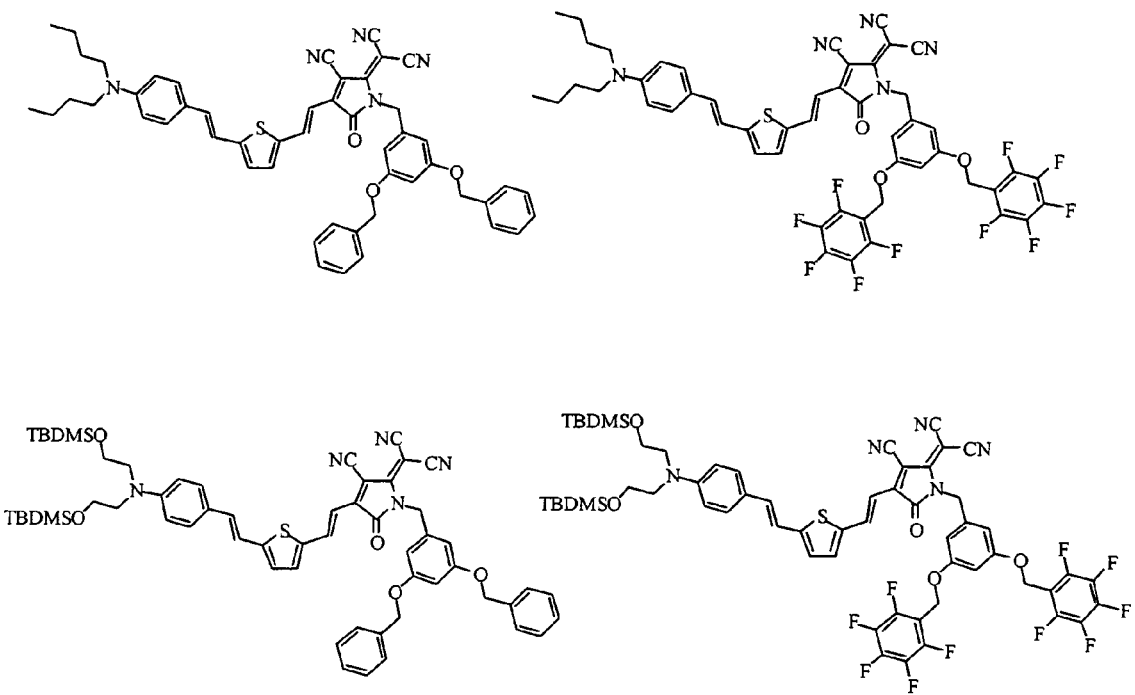
FIG. 23 is an illustration of the chemical structures of four representative pyrroline-containing chromophores of the invention.

The NLO chromophores of the invention having pyrrolizine electron acceptor groups can be prepared from pyrroline acceptor-containing chromophores. Methods for preparing the pyrrolizine acceptor-containing chromophores are illustrated schematically in FIGS. 19 and 20. Referring to FIGS. 19 and 20, cyclization of a representative N-substituted pyrroline-containing chromophore (i.e., N-substitution is —CH($R_3$)($R_4$)) provides representative pyrrolizine-containing chromophores. Alternatively, representative pyrroline-containing chromophores of the invention can be prepared by reaction with a halo-substituted pyrrolizine compound as illustrated schematically in FIG. 20. The preparation of three representative pyrrolizine-containing chromophores is illustrated in FIG. 21.

Pyrrolizine-containing chromophore 23 (see FIG. 21) shows an absorbance maxima at 692 nm in dioxane (parent TCP chromophore has an absorbance maxima at 671 nm in dioxane). Pyrrolizine-containing chromophore 23 in amorphous polycarbonate (APC) matrix exhibited a $r_{33}$ value of 49 pm/V with 25 wt % loading density when poled for 5 minutes with 150 V/μm at 1.3 μm. Isothermal heating and DSC experiments showed that chromophore 23 melted at 218° C. followed by decomposition at 219° C.

The chemical structures of five representative pyrrolizine-containing chromophores of the invention are illustrated in FIG. 22.

Chromophore-Containing Materials and Related Devices

In other aspects of the invention, materials (e.g., lattices) that include the nonlinear optical chromophores and devices that include the nonlinear optical chromophores are provided.

The materials and methods described herein can be useful in a variety of electro-optic applications.

The use of organic polymers in integrated optics and optical communication systems containing optical fibers and routers has been previously described. The compounds, molecular components, polymers, and compositions (hereinafter, "materials") may be used in place of currently used materials, such as lithium niobate, in most type of integrated optics devices, optical computing applications, and optical communication systems. For instance, the materials may be fabricated into switches, modulators, waveguides, or other electro-optical devices.

For example, in optical communication systems devices fabricated from the chromophores of the invention may be incorporated into routers for optical communication systems or waveguides for optical communication systems of for optical switching or computing applications. Because the materials are generally less demanding than currently used materials, devices made from such chromophores may be more highly integrated, as described in U.S. Pat. No. 6,049,641, which is incorporated herein by reference. Additionally, such materials may be used in periodically poled applications as well as certain displays, as described in U.S. Pat. No. 5,911,018, which is incorporated herein by reference.

Techniques to prepare components of optical communication systems from optically transmissive materials have been previously described, and may be utilized to prepare such components from materials provided by the present invention. Many articles and patents describe suitable techniques, and reference other articles and patents that described suitable techniques, where the following articles and patents are exemplary:

Eldada, L. and L. Shacklette, "Advances in Polymer Integrated Optics," *IEEE Journal of Selected Topics in Quantum Electronics* 6(1):54-68, January/February 2000; Wooten, E. L., et al. "A Review of Lithium Niobate Modulators for Fiber-Optic Communication Systems," *IEEE Journal of Selected Topics in Quantum Electronics* 6(1):69-82, January/February 2000; Heismann, F., et al. "Lithium Niobate Integrated Optics: Selected Contemporary Devices and System Applications," *Optical Fiber Telecommunications III B*, Academic, Kaminow and Koch (eds.), New York, 1997, pp. 377-462; Murphy, E., "Photonic Switching," *Optical Fiber Telecommunications III B*, Academic, Kaminow and Koch (eds.), New York, 1997, pp. 463-501; E. Murphy, *Integrated Optical Circuits and Components: Design and Applications.*, Marcel Dekker, New York, Aug. 1999; Dalton, L., et al., "Polymeric Electro-Optic Modulators: From Chromophore Design to Integration with Semiconductor Very Large Scale Integration Electronics and Silica Fiber Optics," *Ind. Eng. Chem. Res.* 38:8-33, 1999; Dalton, L., et al., "From Molecules to Opto-Chips: Organic Electro-Optic Materials," *J. Mater. Chem.* 9:1950-1920, 1999; Liakatas, I. et al., "Importance of Intermolecular Interactions in the Nonlinear Optical Properties of Poled Polymers," *Applied Physics Letters* 76(11): 1368-1370, Mar. 13, 2000; Cai. C., et al., "Donor-Acceptor-Substituted Phenylethenyl Bithiophenes: Highly Efficient and Stable Nonlinear Optical Chromophores," *Organic Letters* 1(11):1847-1849, 1999; Razna, J., et al., "NLO Properties of Polymeric Langmuir-Blodgett Films of Sulfonamide-Substituted Azobenzenes," *J. of Materials Chemistry* 9:1693-1698, 1999; Van den Broeck, K., et al., "Synthesis and Nonlinear Optical Properties of High Glass Transition Polyimides," *Macromol. Chem. Phys* 200:2629-2635, 1999; Jiang, H., and A. K. Kakkar, "Functionalized Siloxane-Linked Polymers for Second-Order Nonlinear Optics," *Macromolecules* 31:2508, 1998; Jen, A. K.-Y., "High-Performance Polyquinolines with Pendent High-Temperature Chromophores for Second-Order Nonlinear Optics," *Chem. Mater.* 10:471-473, 1998; "Nonlinear Optics of Organic Molecules and Polymers," Hari Singh Nalwa and Seizo Miyata (eds.), CRC Press, 1997; Cheng Zhang, Ph.D. Dissertation, University of Southern California, 1999; Galina Todorova, Ph.D. Dissertation, University of Southern California, 2000; U.S. Pat. Nos. 5,272,218; 5,276,745; 5,286,872; 5,288,816; 5,290,485; 5,290,630; 5,290,824; 5,291,574; 5,298,588; 5,310,918; 5,312,565; 5,322,986; 5,326,661; 5,334,333; 5,338,481; 5,352,566; 5,354,511; 5,359,072; 5,360,582; 5,371,173; 5,371,817; 5,374,734; 5,381,507; 5,383,050; 5,384,378; 5,384,883; 5,387,629; 5,395,556; 5,397,508; 5,397,642; 5,399,664; 5,403,936; 5,405,926; 5,406,406; 5,407,009; 5,410,630; 5,414,791; 5,418,871; 5,420,172; 5,443,895; 5,434,699; 5,442,089; 5,443,758; 5,445,854; 5,447,662; 5,460,907; 5,465,310; 5,466,397; 5,467,421; 5,483,005; 5,484,550; 5,484,821; 5,500,156; 5,501,821; 5,507,974; 5,514,799; 5,514,807; 5,517,350; 5,520,968; 5,521,277; 5,526,450; 5,532,320; 5,534,201; 5,534,613; 5,535,048; 5,536,866; 5,547,705; 5,547,763; 5,557,699; 5,561,733; 5,578,251; 5,588,083; 5,594,075; 5,604,038; 5,604,292; 5,605,726; 5,612,387; 5,622,654; 5,633,337; 5,637,717; 5,649,045; 5,663,308; 5,670,090; 5,670,091; 5,670,603; 5,676,884; 5,679,763; 5,688,906; 5,693,744; 5,707,544; 5,714,304; 5,718,845; 5,726,317; 5,729,641; 5,736,592; 5,738,806; 5,741,442; 5,745,613; 5,746,949; 5,759,447; 5,764,820; 5,770,121; 5,76,374; 5,776,375; 5,777,089; 5,783,306; 5,783,649; 5,800,733; 5,804,101; 5,807,974; 5,811,507; 5,830,988; 5,831,259; 5,834,100; 5,834,575; 5,837,783; 5,844,052; 5,847,032; 5,851,424; 5,851,427; 5,856,384; 5,861,976; 5,862,276; 5,872,882; 5,881,083; 5,882,785; 5,883,259; 5,889,131; 5,892,857; 5,901,259; 5,903,330; 5,908,916; 5,930,017; 5,930,412; 5,935,491; 5,937,115; 5,937,341; 5,940,417; 5,943,154; 5,943,464; 5,948,322; 5,948,915; 5,949,943; 5,953,469; 5,959,159; 5,959,756; 5,962,658; 5,963,683; 5,955,233; 5,970,185; 5,970,186; 5,982,958; 5,982,961; 5,985,084; 5,987,202; 5,993,700; 6,001,958; 6,005,058; 6,005,707; 6,013,748; 6,017,470; 6,020,457; 6,022,671; 6,025,453; 6,026,205; 6,033,773; 6,033,774; 6,037,105; 6,041,157; 6,045,888; 6,047,095; 6,048,928; 6,051,722; 6,061,481; 6,061,487; 6,067,186; 6,072,920; 6,081,632; 6,081,634; 6,081,794; 6,086,794; 6,090,332; and 6,091,879.

The forgoing references provide instruction and guidance to fabriacte waveguides from materials generally of the types described herein using approaches such as direct photolithography, reactive ion etching, excimer laser ablation, molding, conventional mask photolithography, ablative laser writing, or embossing (e.g., soft embossing). The foregoing references also disclose electron donors and electron bridges that may be incorporated into the chromophores of the invention or that may also incorporate an electron donor and/or electron bridges described herein.

Components of optical communication systems that may be fabricated, in whole or part, with materials according to the present invention include, without limitation, straight waveguides, bends, single-mode splitters, couplers (including directional couplers, MMI couplers, star couplers), routers, filters (including wavelength filters), switches, modulators (optical and electro-optical, e.g., birefringent modulator, the Mach-Zender interferometer, and directional and evanescent coupler), arrays (including long, high-density waveguide arrays), optical interconnects, optochips, single-mode DWDM components, and gratings. The materials described herein may be used with, for example, wafer-level processing, as applied in, for example, vertical cavity surface emitting laser (VCSEL) and CMOS technologies.

In many applications, the materials described herein may be used in lieu of lithium niobate, gallium arsenide, and other inorganic materials that currently find use as light-transmissive materials in optical communication systems.

The materials described herein may be used in telecommunication, data communication, signal processing, information processing, and radar system devices and thus may be used in communication methods relying, at least in part, on the optical transmission of information. Thus, a method according to the present invention may include communicating by transmitting information with light, where the light is transmitted at least in part through a material including a chromophore of the invention or related macrostructure.

The materials of the present invention can be incorporated into various electro-optical devices. Accordingly, in another aspect, the invention provides electro-optic devices including the following:

an electro-optical device comprising a chromophore or related macrostructure according to the present invention;

a waveguide comprising a chromophore or related macrostructure according to the present invention;

an optical switch comprising a chromophore or related macrostructure according to the present invention;

an optical modulator comprising a chromophore or related macrostructure according to the present invention;

an optical coupler comprising a chromophore or related macrostructure according to the present invention;

an optical router comprising a chromophore or related macrostructure according to the present invention;

a communications system comprising a chromophore or related macrostructure according to the present invention;

a method of data transmission comprising transmitting light through or via a chromophore or related macrostructure according to the present invention;

a method of telecommunication comprising transmitting light through or via a chromophore or related macrostructure according to the present invention;

a method of transmitting light comprising directing light through or via a chromophore or related macrostructure according to the present invention;

a method of routing light through an optical system comprising transmitting light through or via a chromophore or related macrostructure according to the present invention;

an interferometric optical modulator or switch, comprising: (1) an input waveguide; (2) an output waveguide; (3) a first leg having a first end and a second end, the first leg being coupled to the input waveguide at the first end and to the output waveguide at the second end; and 4) and a second leg having a first end and a second end, the second leg being coupled to the input waveguide at the first end and to the output waveguide at the second end, wherein at least one of the first and second legs includes a chromophore or related macrostructure according to the present invention;

an optical modulator or switch, comprising (1) an input; (2) an output; (3) a first waveguide extending between the input and output; and (4) a second waveguide aligned to the first waveguide and positioned for evanescent coupling to the first waveguide; wherein at least one of the first and second legs includes a chromophore or related macrostructure according to the present invention, the modulator or switch may further including an electrode positioned to produce an electric field across the first or second waveguide; and an optical router comprising a plurality of switches, wherein each switch includes: (1) an input; (2) an output; (3) a first waveguide extending between the input and output; and (4) a second waveguide aligned to the first waveguide and positioned for evanescent coupling to the first waveguide; wherein at least one of the first and second legs includes a chromophore or related macrostructure according to the present invention, the plurality of switches may optionally be arranged in an array of rows and columns.

The present invention provides a new class of highly polarizable organic chromophores based on a novel electron withdrawing groups with stable conjugation bridges and donor groups. The NLO chromophores that include these electron withdrawing groups provides significant improvements over current NLO chromophores.

The following examples are provided for the purpose of illustrating, not limiting, the present invention.

EXAMPLES

General Method. Solvents and reagents were purchased from Aldrich unless stated otherwise and purified and dried according to standard procedures. $^1$H NMR spectra (300 MHz) were recorded on a Bruker-300FT NMR spectrometer at room temperature. UV-vis spectra were obtained on a Perkin-Elmer Lambda-9-spectrophotometer with 1 cm quartz cell. ESI-MS spectra were recorded on a Bruker Daltonics Esquire ion trap mass spectrometer.

Example 1

Preparation of Representative Pyrroline Electron Acceptor Compound: TCP Acceptor 2

In this example the preparation of a representative pyrroline electron acceptor compound, TCP acceptor 2, is described. The preparation is illustrated in FIG. 3.

Malononitrile dimer (13.2 parts) is reacted with ethyl pyruvate (23.2 parts) in 100 ml of refluxing ethanol for one hour. After the evaporation of ethanol, the reaction mixture was extracted with 500 ml of dichlormethane (major amount of regenerated malonitrile dimer is removed by low solubility of the dimer in dichloromethane) and the acceptor was purified with short column chromatography using the dichloromethane as eluent solvent. The first fraction from the column was concentrated to give 1.84 part of slightly yellowish crystalline TCP acceptor 2. The acceptor dimerized slowly in warm ethanol, but is stable in solid state at room temperature for normal storage. $^1$H NMR (CDCl$_3$, ppm): δ 2.39 (3H, s), δ 8.75 (1H, s).

Example 2

Preparations of Representative Pyrroline Electron Acceptor-Containing Chromophores: TCP Chromophores 6, 7, and 8

Figure 9:
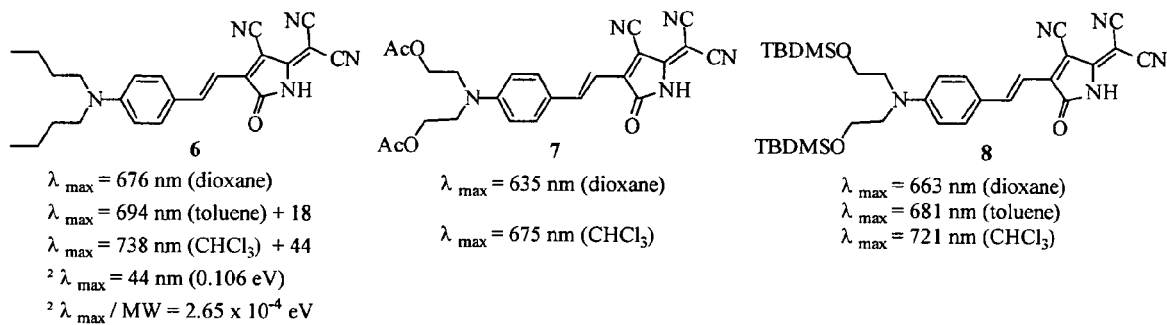
FIG. 9 compares some spectral properties for three representative pyrroline-containing chromophores of the invention.

In this example the preparation of representative pyrroline electron acceptor-containing chromophores, TCP chromophores 6, 7, and 8, is described. The chromophores are illustrated in FIG. 9.

To a solution of ethyl pyruvate (23.2 parts) in 100 ml of ethanol was added malononitrile dimer (13.2 parts) and the mixture was refluxed under argon for one hour. To the reaction mixture was added 4-(diethylamino)benzaldehyde (12.4 parts). The resulting reaction mixture was refluxed under argon for 3 hours to complete the reaction. The reaction mixture was cooled and the solvent was evaporated to one half of its volume and the precipitated products were filtered. The filtered solid was washed with 200 ml of dichloromethane and air dried overnight to give 14 part of green crystalline solid 6. $^1$H NMR (DMSO, ppm): δ 9.30 (1H, d), δ 8.76 (1H, d), δ 7.86 (2H, d), δ 7.77 (1H, d), δ 6.97 (2H, d), δ 4.20 (4H, t), δ 3.74 (4H, t), δ 1.97 (6H, s). UV-vis spectra: $\lambda_{max,\ dioxane}$=671 nm, $\lambda_{max,\ toluene}$=691 nm, $\lambda_{max,\ chloroform}$=732 nm. MS m/z (ES) 344.2 (M$^+$, 90%), 315.3 (100%), 300.4 (5%). Chromophores 7 and 8 were synthesized using the above procedure except using 4-diacetoxyethylamino)benzaldehyde and 4-(di-tert-butyldimethylsiloxy) ethylamino) benzaldehyde, respectively, in place of 4-(diethylamino)benzaldehyde. $^1$H NMR (DMSO, ppm): δ 8.38 (1H, d), δ 8.03 (1H, s), δ 7.70 (2H, d), δ 6.94 (1H, d), δ 6.83 (2H, d), δ 2.49 (4H, t), δ 1.55 (4H, m), δ 1.33 (4H, m), δ 0.92 (6H, t); UV-vis spectra: $\lambda_{max, dioxane}$=635 nm, and $\lambda_{max, chloroform}$=675 nm for 7; $^1$H NMR (DMSO, ppm): δ 9.20 (1H, d), δ 8.40 (1H, d), δ 7.70 (2H, d), δ 6.96 (1H, d), δ 6.90 (2H, d), δ 3.60 (4H, t), δ 3.50 (4H, t), δ 0.90 (18H, s), δ 0.05 (12H, t); UV-vis spectra: $\lambda_{max, dioxane}$=663 nm, $\lambda_{max, toluene}$=681 nm, $\lambda_{max, chloroform}$=721 nm for 8.

Example 3

Preparation of a Representative Pyrroline Electron Acceptor-Containing Chromophore: TCP Chromophore 6

In this example the preparation of a representative pyrroline electron acceptor-containing chromophore, TCP chromophore 6, is described.

To a solution of acceptor 2 (1.8 parts), prepared as described in Example 1, in 20 ml of ethanol was added 4-(diethylamino)benzaldehyde (2.3 parts) and the mixture was refluxed under argon for half hour to complete the reaction. The resulting reaction mixture was cooled, filtered, washed with cool ethanol or isopropanol, and dried to give 3.1 part of pure TCP chromophore 6.

Example 4

Preparations of Representative Pyrroline Electron Acceptor-Containing Chromophores: TCP Chromophores 9, 10, 11, and 22

Figure 18:
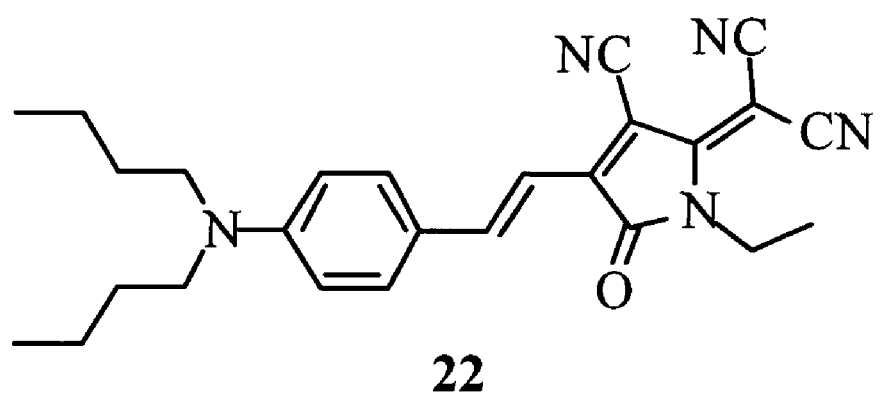
FIG. 18 is an illustration of the chemical structure of a representative pyrroline-containing chromophore of the invention.

In this example the preparations of representative pyrroline electron acceptor-containing chromophores, TCP chromophores 9, 10, 11, and 22, are described. The chromophores are illustrated in FIGS. 10 and 18.

To a solution of (4.0 parts) chromophore 6 (4.0 parts), prepared as described in Example 3, in 50 ml of acetonitrile was added oven dried potassium carbonate (4.1 parts) and the mixture was refluxed under argon for ten minutes. Allyl bromide (2.4 parts) was added to the refluxing mixture followed by continued refluxing for one more hour. The resulting reaction mixture was cooled and the solvent was evaporated using rotary evaporation. The solid residue was extracted with 100 ml of dichloromethane and the chromophore 9 was purified by column chromatography using the dichloromethane as eluent solvent. $^1$H NMR (CDCl$_3$, ppm): δ 8.50 (1H, d), δ 7.59 (2H, d), δ 7.02 (1H, d), δ 6.69 (2H, d), δ 5.90 (1H, m), δ 5.30 (1H, d), δ 5.10 (1H, d), δ 4.67 (2H, d), δ 3.41 (4H, t), δ 1.60 (4H, m), δ 1.50 (4H, m), δ 1.00 (6H, t); UV-vis spectra: $\lambda_{max, dioxane}$=684 nm, $\lambda_{max, toluene}$=697 nm, $\lambda_{max, chloroform}$=741 nm. Chromophores 10 and 11 were synthesized using the above procedure except using ethyl bromo propionate and 4-methoxybenzoyl chloride, respectively, in place of allyl bromide. $^1$H NMR (CDCl$_3$, ppm): δ 8.47 (1H, d), δ 7.59 (2H, d), δ 7.01 (1H, d), δ 6.69 (2H, d), δ 4.80 (2H, s), δ 4.28 (2H, q), δ 3.41 (4H, t), δ 3.41 (4H, t), δ 1.62 (4H, m), δ 1.38 (4H, m), δ 1.31 (3H, t), δ 0.97 (6H, t). UV-vis spectra: $\lambda_{max, dioxane}$=689 nm, $\lambda_{max, toluene}$=703 nm, $\lambda_{max, chloroform}$=746 nm for 10; $^1$H NMR (CDCl$_3$, ppm): δ 8.44 (1H, d), δ 7.92 (2H, d), δ 7.57 (2H, d), δ 6.99 (1H, d), δ 6.98 (2H, d), δ 6.69 (2H, d), δ 3.89 (3H, s), δ 3.42 (4H, t), δ 1.63 (4H, m), δ 1.38 (4H, m), δ 0.97 (6H, t). UV-vis spectra: $\lambda_{max, dioxane}$=690 nm, $\lambda_{max, toluene}$=707 nm, $\lambda_{max, chloroform}$=754 nm for 11. Compound 22 was prepared using the above procedure except using diethyl sulfate in place of allyl bromide.

Example 5

Preparation of a Representative Pyrroline Electron Acceptor-Containing Chromophore: TCP Chromophore 12

In this example the preparation of a representative pyrroline electron acceptor-containing chromophore, TCP chromophore 12, is described.

To a solution of 4-(dibutylamino)phenyl thiophene (2.9 parts) in 20 ml of DMF was slowly added 3-chloro-4-cyano-5-dicyanomethylene-2-oxo-3-pyrroline (TCP chloride) (2.0 parts). The reaction mixture was stirred under argon overnight at room temperature. The mixture was poured into 100 ml of ice water, and the mixture was stirred to warmup to room temperature. The dark green solid was filtered, washed, and dried. Chromophore 12 was purified by column chromatography using 30% ethylacetate in hexane as eluent solvent. $^1$H NMR (DMSO, ppm): δ 8.32 (2H, d), δ 7.68 (1H, d), δ 6.96 (2H, d), δ 6.75 (1H, d), δ 3.50 (4H, t), δ 1.54 (4H, m), δ 1.33 (4H, m), δ 0.91 (6H, t); UV-vis spectra: $\lambda_{max, dioxane}$=705 nm, $\lambda_{max, toluene}$=731 nm, $\lambda_{max, chloroform}$=780 nm for 12.

Example 6

Preparation of a Representative Pyrroline Electron Acceptor-Containing Chromophore: TCP Chromophore 13

In this example the preparation of a representative pyrroline electron acceptor-containing chromophore, TCP chromophore 13, is described.

To a solution of ethyl pyruvate (11.6 parts) in 100 ml of ethanol was added malononitrile dimer (6.6 parts) and the mixture was refluxed under argon for one hour. Aldehyde 16 (12.0 parts), prepared as described in Example 8, was added to the reaction mixture and the reaction mixture was refluxed under argon for 3 hours to complete the reaction. The reaction mixture was cooled and the solvent was evaporated and the solid mixture was chromatographed over silica gel using 30% ethyl acetate in hexane to give 7.1 part of chromophore 17. $^1$H NMR (CDCl$_3$, ppm): δ 8.55 (1H, d), δ 7.40 (2H, d), δ 7.15 (1H, d), δ 7.05 (1H, d), δ 6.85 (1H, d), δ 6.65 (1H, d), δ 6.60 (1H, d), δ 6.40 (2H, d), δ 3.35 (4H, t), δ 1.60 (4H, m), δ 1.40 (4H, m), δ 0.99 (6H, t), UV-vis spectra: $\lambda_{max, dioxane}$=764 nm, $\lambda_{max, toluene}$=807 nm, $\lambda_{max, chloroform}$=875 nm.

Example 7

Preparation of a Representative Pyrroline Electron Acceptor-Containing Chromophore: TCP Chromophore 13

In this example the preparation of a representative pyrroline electron acceptor-containing chromophore, TCP chromophore 13, is described.

To a solution of acceptor 2 (1.8 parts), prepared as described in Example 1, in 20 ml ethanol was added aldehyde 16 (3.4 parts), prepared as described in Example 8, and the mixture was refluxed under argon for half hour to complete the reaction. The resulting reaction mixture is cooled, filtered, washed with cool ethanol or isopropanol, and dried to give 4.0 part of chromophore 13.

Many of TCP chromophores with extended donor conjugation bridges such as chromophore 14 can be synthesized using the above procedure starting from proper donor conjugation bridges with terminal aldehyde group in place of aldehyde 16. $^1$H NMR (CDCl$_3$, ppm): δ 8.54 (1H, d), δ 7.80~6.8 (7H, m), δ 5.80 (1H, m), δ 5.30 (1H, d), δ 5.10 (1H, d), δ 4.65 (2H, s), δ 3.30 (4H, m), δ 1.60 (4H, m), δ 1.40 (4H, m), δ 1.00 (6H, m). UV-vis spectra: $\lambda_{max, \, dioxane}$=748 nm, $\lambda_{max, \, toluene}$=800 nm, $\lambda_{max, \, chloroform}$=838 nm for 14.

Example 8

Preparation of a Representative Pyrroline Electron Acceptor-Containing Chromophore: TCP Chromophore 15

In this example the preparation of a representative pyrroline electron acceptor-containing chromophore, TCP chromophore 15, is described. The preparation is illustrated schematically in FIG. 15.

Dendronized benzoic acid (1.0 part), prepared from pentafluorobenzyl bromide and 3,5-dihydroxy benzoic acid, was added to 10 mL dry dichloromethane and 2 ml thionyl chloride was added dropwise. The dendronized benzoic acid dissolved gradually. The reaction mixture was allowed to stir under nitrogen at room temperature for overnight. The solvent was evaporated to give 1.0 part of compound 17 as white solid, which can be used for next step without further purification.

Chromophore 13 (10 parts), prepared as described in Example 7, and potassium carbonate (1 part) was added to 100 ml dry acetonitrile. The mixture was heated to reflux for 10 min under nitrogen. Dendronized benzoyl chloride 17 (15.7 part) was added. The reaction mixture was then stirred at this temperature for 30 min. After rotary evaporation to remove the solvent, the crude product was purified by flash chromatography to afford 1.0 part of chromophore 15 as black solid. $^1$H NMR (CDCl$_3$, ppm): δ 8.45 (1H, d), δ 7.40~6.60 (12H, m), δ 3.33 (4H, t), δ 1.55 (1H, d), δ 1.55 (4H, m), δ 1.35 (4H, m), δ 0.95 (6H, t). UV-vis spectra: $\lambda_{max, \, chloroform}$=875 nm. MS m/z (ES) 1004.4 (M$^+$, 8%), 960.7 (100%), 947.5 (15%), 919.3 (10%), 497.2 (17%).

Example 9

Preparations of Representative Pyrroline Electron Acceptor-Containing Chromophores: TCP Chromophores 18, 19, 20, and 21

In this example the preparations of representative pyrroline electron acceptor-containing chromophores, TCP chromophores 18, 19, 20, and 21, is described. The chromophores are illustrated in FIG. 16.

Chromophore 18 was prepared using the procedure described in Example 7. Chromophore 19 was prepared using the procedure described in Example 4 starting from chromophore 18. Chromophore 20 was prepared by acidic hydrolysis of chromophore 19. Chromophore 21 was prepared by acylation of chromophore 20 using pentafluorobenzoyl chloride in dichloromethane.

Example 10

Electro-Optical Properties of Representative Chromophores

In this example, the electro-optical properties of representative chromophores of the invention, chromophores 11, 15, 19, and 21, are described.

To determine the macroscopic NLO properties of representative TCP chromophores, EO studies were performed on a guest/host polymer system in which chromophore 11, prepared as described in Example 4, was formulated in amorphous polycarbonate (APC) from Aldrich Chemical Inc. A cyclopentanone solution of chromophore 11 and APC with 10 wt % was filtered through 0.2 mm PTFE syringe filter and then was spin-coated onto half-etched ITO glass substrates at a spread of 500 rpm and spin rate of 1000 rpm. The resulting film showed good optical quality with a thickness of 1.5 μm. The film was soft-baked under vacuum at 65° C. for 12 hours to ensure the removal of the residual solvent. A thin layer of gold was sputtered onto the film as the top electrode to perform the electric field poling. The film was contact poled at 135° C. for 5 minutes with a DC electric field of 100 V/μm under nitrogen atmosphere. The EO coefficient ($r_{33}$) value was measured using the simple reflection technique at 1.3 μm and the poled film of chromophore 11 showed an optical $r_{33}$ value of 9 pm/V. In a similar manner, EO measurements were performed on the amorphous polycarbonate doped with chromophore 15 (20 wt %), prepared as described in Example 8. The solution of the chromophore in cyclopentanone (15% w/w, filtered through a 0.2 μm syringe filter) was spin-coated onto the indium tin oxide (ITO) glass substrates. The film was baked under vacuum at 85° C. overnight to remove the residual solvent. A thin layer of gold was sputtered onto the film as the top electrode for poling. The sample was then poled at 110° C. with an applied DC electric field of 65 V/μm for 10 minutes. The $r_{33}$ value for the chromophore 15 film was measured to be 51 pm/V at 1.5 μm using the simple reflection technique. Chromophores 19 and 21 were similarly treated. Moreover, chromophore 19 showed $r_{33}$ value of 22 pm/V with 20 wt % loading density in APC host when poled with 10 V/μm at 1.3 μm, and the chromophore 21 showed $r_{33}$ value of 29 pm/V with 25 wt % loading density in PMMA host when poled with 10 V/μm at 1.3 μm.

Example 11

Thermal Properties of Representative Chromophores

In this example, the thermal properties of chromophores 3, 4, and 5, are described.

Polymer composites in host/guest system were prepared by doping 10 wt % of chromophore 3, 4, and 5 into PQ-100. Spin-coated films on glass substrate were heated at 170° C. for 20 minutes under nitrogen atmosphere. The π-π* charge-transfer bands in absorption spectra were used to monitor and compare the degradation/sublimation of the chromophores in the polymer matrix.

Figure 17:
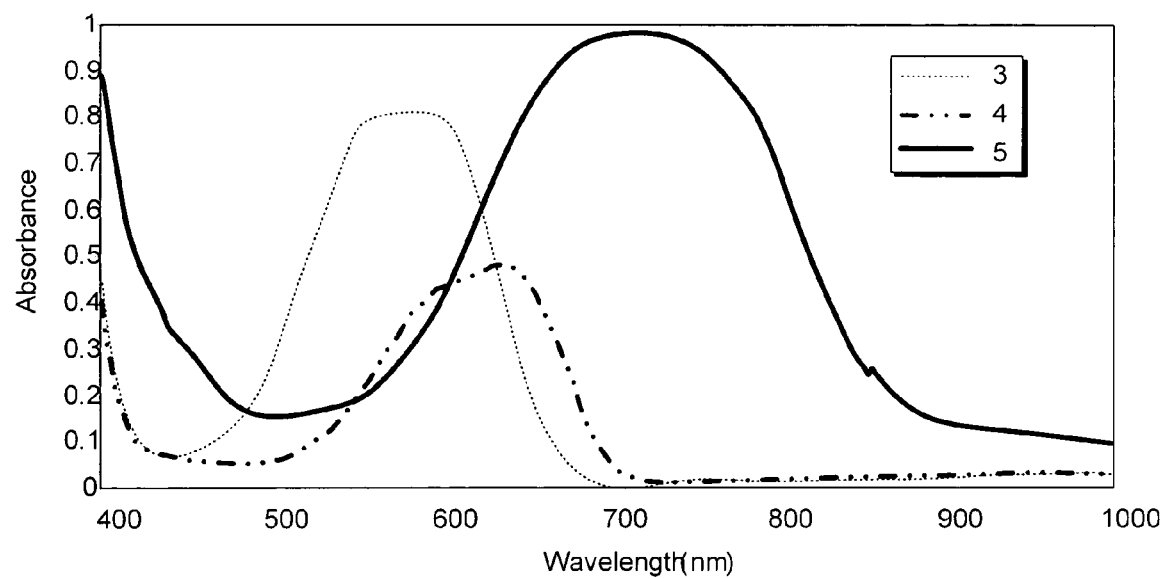
FIG. 17 is a graph comparing the isothermal heating properties of three pyrroline-containing chromophores.

The results are illustrated graphically in FIG. 17.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A compound having the formula

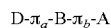

where D is selected from a group consisting of N,N-disubstituted amino phenyl and N,N-disubstituted amino thiophenyl group, B is selected from the group consisting of substituted or unsubstituted thiophene group, substituted or unsubstituted fused dithiophene, and substituted or unsubstituted thiazole, $\pi_a$ is optional and represents a group that conjugates D to B, $\pi_b$ is a group that conjugates B to A and wherein A has the formula

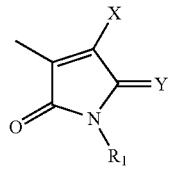

wherein X is cyano;

wherein Y is $C(X_a)(X_b)$, where $X_a$ and $X_b$ are CN; and wherein $R_1$ is substituted or unsubstituted alkyl; substituted or unsubstituted aryl; or —C(=O)$R_2$, where $R_2$ is substituted or unsubstituted alkyl, or substituted or unsubstituted aryl.

2. The compound of claim 1, wherein D is an N,N-disubstituted amino phenyl group.

3. The compound of claim 1, wherein D is an N,N-disubstituted amino thiophenyl group.

4. The compound of claim 1, wherein B is selected from the group consisting of a thiophene and a substituted thiophene group.

5. The compound of claim 1, wherein B is selected from the group consisting of a fused dithiophene and a substituted fused dithiophene group.

6. The compound of claim 1, wherein B is selected from the group consisting of a thiazole and a substituted thiazole group.

7. A compound having the formula:

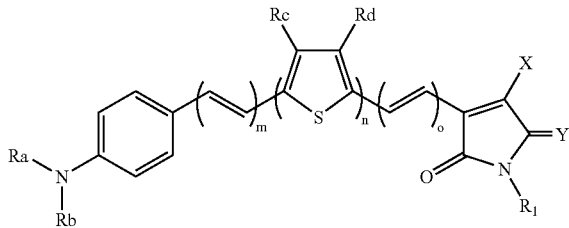

wherein m=0, 1, or 2;

wherein n=1, 2, 3, 4, 5, or 6;

wherein o=0, 1, or 2;

wherein when X is CN, Y is C(CN)$_2$, and m=1 or 2, n is $\geq 1$;

wherein $R_a$, $R_b$, $R_c$, and $R_d$ are independently selected from hydrogen, substituted or unsubstituted alkyl, and unsubstituted aryl, wherein X is hydrogen; fluorine; chlorine; bromine; cyano; substituted or unsubstituted alkyl; perfluoroalkyl; substituted or unsubstituted aryl; —C(=O)O$R_2$, where $R_2$ is substituted or unsubstituted alkyl, or substituted or unsubstituted aryl; —C(=O)N$R_{2a}R_{2b}$, where $R_{2a}$ and $R_{2b}$ are independently hydrogen, substituted or unsubstituted alkyl, substituted or unsubstituted aryl; —SO$_2$R$_2$, where $R_2$ is substituted or unsubstituted alkyl, or substituted or unsubstituted aryl; or —P(=O)(OR$_{2a}$)(OR$_{2b}$), where $R_{2a}$ and $R_{2b}$ are independently hydrogen, substituted or unsubstituted alkyl, or substituted or unsubstituted aryl;

wherein Y is O, S, NR$_3$, C(R$_{3a}$)(R$_{3b}$), Si(R$_{3a}$)(R$_{3b}$), or C(X$_a$)(X$_b$), where R$_3$ is hydrogen, substituted or unsubstituted alkyl, or substituted or unsubstituted aryl, where R$_{3a}$ and R$_{3b}$ are independently hydrogen, substituted or unsubstituted alkyl, or substituted or unsubstituted aryl, and where X$_a$ and X$_b$ are independently selected from X; and wherein R$_1$ is hydrogen; substituted or unsubstituted alkyl; substituted or unsubstituted aryl; or —C(=O)R$_2$, where R$_2$ is susbtituted or unsubstituted alkyl, or substituted or unsubstituted aryl.

8. A compound having the formula:

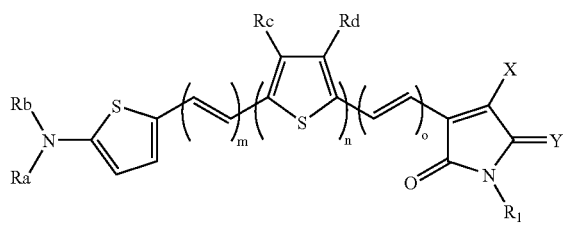

wherein m=0, 1, or 2;

wherein n=1, 2, 3, 4, 5, or 6;

wherein o=0, 1, or 2;

wherein $R_a$, $R_b$, $R_c$, and $R_d$ are independently selected from hydrogen, substituted or unsubstituted alkyl, and substituted and unsubstituted aryl, wherein X is hydrogen; fluorine; chlorine; bromine; cyano; substituted or unsubstituted alkyl; perfluoroalkyl; substituted or unsubstituted aryl; —C(=O)OR$_2$, where R$_2$ is substituted or unsubstituted alkyl, or substituted or unsubstituted aryl; —C(=O)NR$_{2a}$R$_{2b}$, where R$_{2a}$ and R$_{2b}$ are independently hydrogen, substituted or unsubstituted alkyl, or substituted or unsubstituted aryl; —SO$_2$R$_2$, where R$_2$ is substituted or unsubstituted alkyl, or substituted or unsubstituted aryl; or —P(=O)(OR$_{2a}$)(OR$_{2b}$), where R$_{2a}$ and R$_{2b}$ are independently hydrogen, substituted or unsubstituted alkyl, or substituted or unsubstituted aryl;

wherein Y is O, S, NR$_3$, C(R$_{3a}$)(R$_{3b}$), Si(R$_{3a}$)(R$_{3b}$), or C(X$_a$)(X$_b$), where R$_3$ is hydrogen, substituted or unsubstituted alkyl, or substituted or unsubstituted aryl, where R$_{3a}$ and R$_{3b}$ are independently hydrogen, substituted or unsubstituted alkyl, or substituted or unsubstituted aryl, and where X$_a$ and X$_b$ are independently selected from X; and wherein R$_1$ is hydrogen; substituted or unsubstituted alkyl; substituted or unsubstituted aryl; or —C(=O)R$_2$, where R$_2$ is substituted or unsubstituted alkyl, or substituted or unsubstituted aryl.

* * * * *

UNITED STATES PATENT AND TRADEMARK OFFICE
CERTIFICATE OF CORRECTION

PATENT NO. : 7,307,173 B1  Page 1 of 1
APPLICATION NO. : 11/064420
DATED : December 11, 2007
INVENTOR(S) : K.-Y. Jen et al.

It is certified that error appears in the above-identified patent and that said Letters Patent is hereby corrected as shown below:

| COLUMN | LINE | ERROR |
|---|---|---|
| 25 (Claim 7, | 55 line 10) | before "unsubstituted" insert --substituted and-- |
| 26 (Claim 7, | 16 line 32) | "susbtituted" should read --substituted-- |

Signed and Sealed this

Twenty-ninth Day of April, 2008

JON W. DUDAS
*Director of the United States Patent and Trademark Office*

UNITED STATES PATENT AND TRADEMARK OFFICE
CERTIFICATE OF CORRECTION

PATENT NO. : 7,307,173 B1
APPLICATION NO. : 11/064420
DATED : December 11, 2007
INVENTOR(S) : K.-Y. Jen et al.

It is certified that error appears in the above-identified patent and that said Letters Patent is hereby corrected as shown below:

| COLUMN | LINE | ERROR |
|---|---|---|
| 1 | 13 | Replace the paragraph following the title "STATEMENT OF GOVERNMENT LICENSE RIGHTS", with the following: |
| | | --This invention was made with U.S. Government support under grant number DMR-0120967 awarded by the National Science Foundation and under grant number MDA972-02-1-0009 awarded by the U.S. Army Medical Research Acquisition Activity. The U.S. Government has certain rights in this invention.-- |

Signed and Sealed this

Seventeenth Day of March, 2009

JOHN DOLL
*Acting Director of the United States Patent and Trademark Office*